(12) United States Patent
Wukusick et al.

(10) Patent No.: US 7,207,472 B2
(45) Date of Patent: Apr. 24, 2007

(54) CARTRIDGE WITH LOCKING KNIFE FOR A CURVED CUTTER STAPLER

(75) Inventors: Peter Michael Wukusick, Batesville, IN (US); Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 46 days.

(21) Appl. No.: 11/014,896

(22) Filed: Dec. 20, 2004

(65) Prior Publication Data

US 2005/0139635 A1    Jun. 30, 2005

Related U.S. Application Data

(60) Provisional application No. 60/532,911, filed on Dec. 30, 2003.

(51) Int. Cl.
*A61B 17/04* (2006.01)
*A61B 17/11* (2006.01)

(52) U.S. Cl. ............... 227/181.1; 227/19; 227/180.1; 227/176.1; 227/178.1

(58) Field of Classification Search ............... 227/19, 227/181.1, 180.1, 176.1, 178.1
See application file for complete search history.

(56) References Cited

U.S. PATENT DOCUMENTS

| | | | | |
|---|---|---|---|---|
| 3,740,994 A | * | 6/1973 | De Carlo, Jr. ............... 72/407 |
| 4,304,236 A | * | 12/1981 | Conta et al. ............... 227/179.1 |
| 4,520,817 A | * | 6/1985 | Green ............... 227/176.1 |
| 5,100,042 A | * | 3/1992 | Gravener et al. ............... 227/176.1 |
| 5,352,238 A | * | 10/1994 | Green et al. ............... 606/220 |
| 6,805,273 B2 | * | 10/2004 | Bilotti et al. ............... 227/180.1 |
| 2005/0139634 A1 | * | 6/2005 | Schwemberger et al. 227/180.1 |

OTHER PUBLICATIONS

U.S. Appl. No. 11/014,897, Replaceable Cartridge Module for a Surgical Stapling and Cutting Instrument.
U.S. Appl. No. 11/015,278, Retaining Pin Lever Advancement Mechanism for a Curved Cutter Stapler.
U.S. Appl. No. 11/014,906, Closure Plate Lockout for a Curved Cutter Stapler.
U.S. Appl. No. 11/014,913, Cartridge Retainer for a Curved Cutler Stapler.
U.S. Appl. No. 11/014,909, Curved Cutler Stapler with Aligned Tissue Retention Feature.
U.S. Appl. No. 11/014,910, Specific Curvature of Curved Stapler to Fit Male Pelvis.
U.S. Appl. No. 11/014,914, Slotted Pins to Guide Knife and Reduce Cutting Tags.
U.S. Appl. No. 11/014,895, Knife Refraction Arm for a Curved Cutler Stapler.

* cited by examiner

*Primary Examiner*—Brian Nash
(74) *Attorney, Agent, or Firm*—Welsh & Flaxman LLC

(57) ABSTRACT

A surgical instrument adapted for applying a plurality of surgical fasteners to body tissue includes a cartridge module having a cartridge housing containing a plurality of surgical fasteners and a knife. The cartridge module includes a driver disposed to push surgical fasteners out of the cartridge housing. The instrument also includes a firing mechanism associated with the cartridge housing for ejecting the surgical fasteners and the knife from the cartridge housing. The knife includes a detent disposed to contact a mating detent of the cartridge module during longitudinal travel of the knife thereby preventing undesired forward and rearward motion of the knife. The driver includes a detent disposed to contact at least one mating detent formed on the cartridge module.

31 Claims, 36 Drawing Sheets

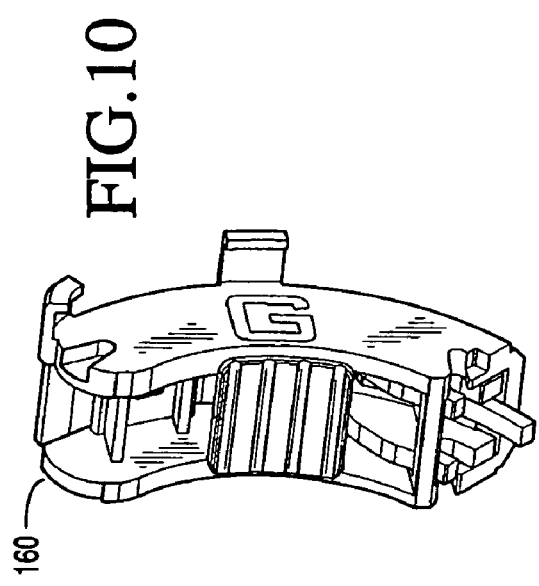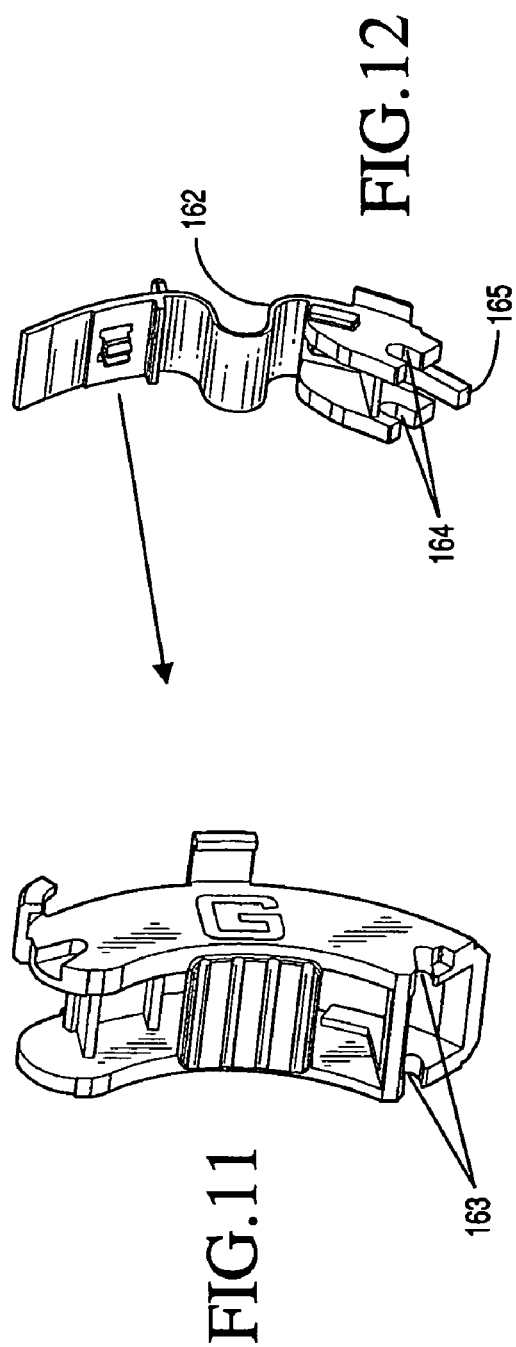

CARTRIDGE WITH LOCKING KNIFE FOR A CURVED CUTTER STAPLER

CROSS REFERENCE TO RELATED APPLICATION

This application is based upon U.S. Provisional Patent Application No. 60/532,911, filed Dec. 30, 2003, entitled "STAPLER CARTRIDGE FOR A CURVED CUTTER STAPLER".

BACKGROUND OF THE INVENTION

1. Field of the Invention

The present invention relates to a surgical stapling and cutting instrument adapted for use in the diagnosis and therapy of pathologies treated by stapled resection. More particularly, the invention relates to a cartridge module for surgical stapling and cutting instruments that includes detents for the driver and knife assemblies.

2. Description of the Prior Art

Surgical stapling and cutting instruments are commonly utilized in the diagnosis and treatment of pathologies treated by stapled resection. Surgical stapling and cutting instruments provide a mechanism to extend the transluminal exploitation of mechanical suturing devices introduced via the anal canal, mouth, stomach and service accesses. Although surgical stapling and cutting instruments are most commonly utilized with rectal pathologies, surgical stapling and cutting instruments may be used in a variety of environments.

Over time, surgical stapling and cutting instruments have been developed. These instruments generally include a support frame, an anvil attached to the support frame and a cartridge housing carrying a plurality of staples. The instruments also include a driver within the cartridge housing which pushes all of the staples out simultaneously into the anvil to form the staples into a generally B-shape, suturing tissue together. In addition, these instruments include approximation mechanisms for moving the cartridge housing from a spaced position from the anvil to accept tissue therebetween to a closed position where the tissue is clamped between the anvil and the cartridge housing. Finally, the devices include a firing means for moving the driver forward to form the staples against the anvil.

Many of these instruments rely upon replaceable cartridge modules including a plurality of staples. These replaceable cartridges permit multiple usage of surgical stapling and cutting instruments by simply replacing the cartridge modules after each staple procedure. Most cartridge modules include a staple driver and a knife assembly. Both assemblies slide within the cartridge housing when the device is fired. Prior to use, the staple driver assembly and the knife assembly must be held in a retracted position within the cartridge module. The structure holding the staple driver assembly and knife assembly in this position must be strong enough to prevent movement during shipping. Movement of the staples out of their pockets may lead to staples falling out or being out of position, both of which may lead to bleeding staple lines or worse. Movement of the knife assembly to a position where the knife is exposed might cause injury to anyone using the device or an inadvertent cut in tissue during use on a patient.

After firing of the cartridge module, the staple driver assembly must remain in its forward fired position. The stapler driver assembly is retained in this position to ensure that the spent cartridge lockout assembly is activated. The staple driver assembly is also retained in this position such that the driver tips remain visible providing the user with a visible clue that the cartridge module is spent.

The knife assembly must be retracted and held within the cartridge housing after the device is fired and the trigger is released. The structure that holds the knife assembly in the retracted position must withstand the forces experienced during reloading so that the knife cutting edge is not exposed.

Since the cartridge module may be fired several times during manufacturing, the structures that hold the driver assembly and the knife assembly within the cartridge module must be durable enough to withstand repeated cycling. The force required to reset the staple driver assembly and the knife assembly to the retracted positions should also be minimized to ease manufacturing and to minimize the knife retraction force requirement (spring force) for the instrument.

With this in mind, an improved cartridge module providing structure for holding and indicating the position of the staple driver assembly and the knife assembly is required. The present invention provides such a cartridge module.

SUMMARY OF THE INVENTION

It is, therefore, an object of the present invention to provide a surgical instrument adapted for applying a plurality of surgical fasteners to body tissue. The surgical instrument includes a cartridge module having a cartridge housing containing a plurality of surgical fasteners and a knife. The cartridge module includes a driver disposed to push surgical fasteners out of the cartridge housing. A firing mechanism is associated with the cartridge housing for ejecting the surgical fasteners and the knife from the cartridge housing. The knife includes a detent disposed to contact a mating detent of the cartridge module during longitudinal travel of the knife thereby preventing undesired forward and rearward motion of the knife. The driver includes a detent disposed to contact at least one mating detent formed on the cartridge module.

It is also an object of the present invention to provide a surgical instrument wherein the cartridge housing includes a cartridge slot through which the detent of the knife extends, the cartridge slot including first and second flexible fingers molded into the side of the cartridge housing.

It is another object of the present invention to provide a surgical instrument wherein the first and second fingers are oriented parallel to the longitudinal axis of the cartridge module.

It is a further object of the present invention to provide a surgical instrument wherein the first finger is shaped and dimensioned to contact the detent of the knife.

It is also another object of the present invention to provide a surgical instrument wherein the second finger is shaped and dimensioned to contact the detent of the driver.

It is still another object of the present invention to provide a surgical instrument wherein cam surfaces are positioned along the edge of each of the first and second fingers.

It is yet another object of the present invention to provide a surgical instrument wherein the location of the respective cam surfaces is determined by the desired position of the driver or knife during operation.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 10, 11 and 12 show the assembly of the retainer.

DESCRIPTION OF THE PREFERRED EMBODIMENTS

Figure 1:
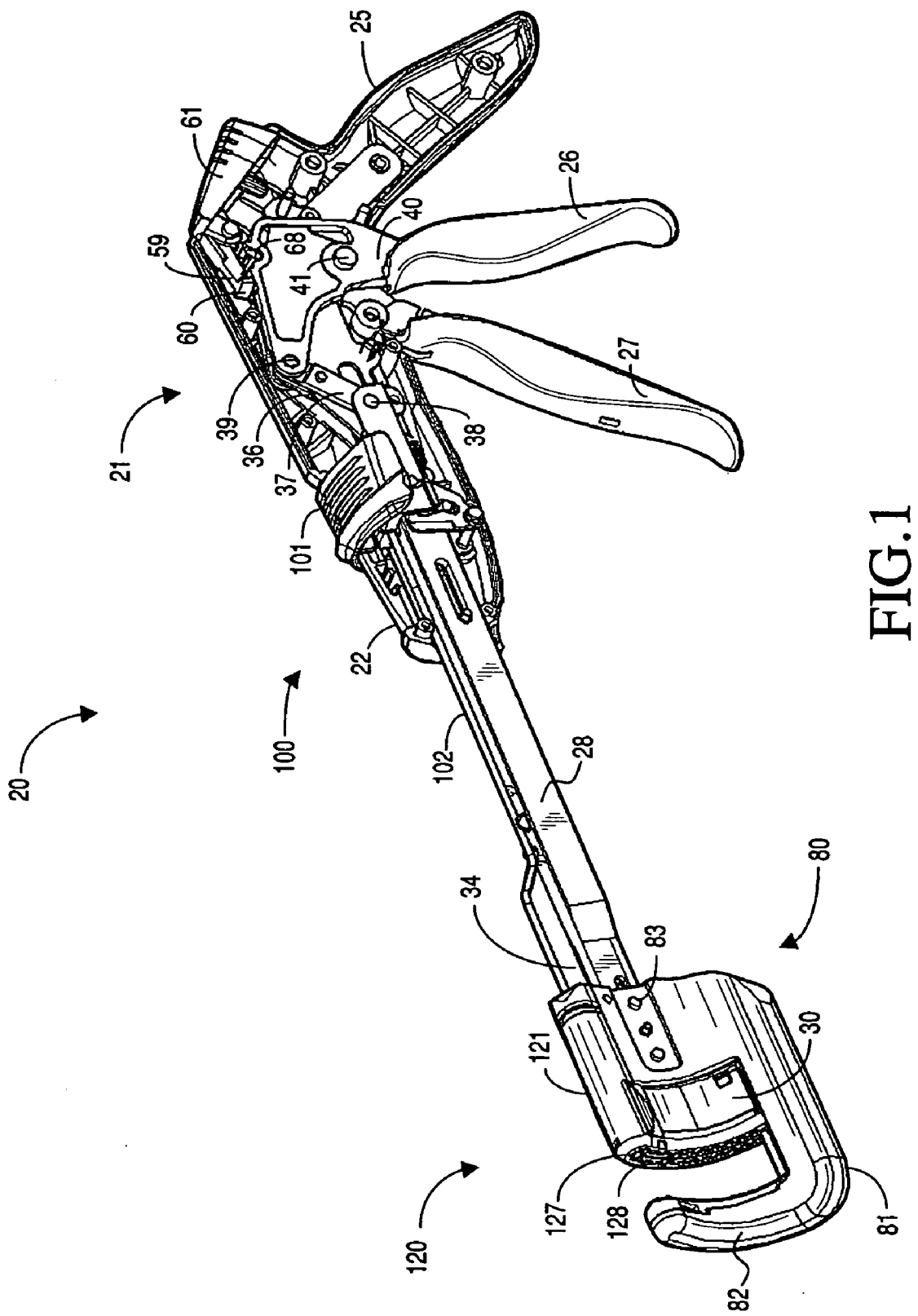
FIG. 1 is a perspective view of the linear surgical stapler in accordance with the present invention.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, a surgical instrument 20 adapted for applying a plurality of surgical fasteners to body tissue is disclosed. The surgical instrument 20 includes an anvil 122 and a cartridge housing 121 containing a plurality of surgical fasteners and a knife 126. The cartridge housing 121 and anvil 122 are relatively movable between a first spaced apart position and a second position in close approximation with one another. The instrument 20 also includes a firing mechanism associated with the cartridge housing 121 for ejecting the surgical fasteners and the knife 126 from the cartridge housing 121 to be driven against the anvil 122. A cartridge module 120, which the cartridge housing 121 forms a part of, includes a driver 131 disposed to push fasteners out of the cartridge housing 121 and a knife holder 130 disposed immediately proximal of the driver 131 in the cartridge housing 121. The knife holder 130 is attached to the knife 126 that extends distally from the knife holder 130 through a slot 200 in the driver and through a slot 199 in the cartridge housing 121. The knife holder 130 includes a detent post 138 that extends through a slot 137 in the cartridge housing 121. The knife holder detent post 138 is disposed to contact a detent protrusion 139 of the cartridge slot 137 during the longitudinal travel of the knife 126 and knife holder 130. The driver 131 includes a detent post 140 that is disposed to contact proximal and distal detent protrusions 141, 142 formed on the cartridge housing slot 137.

Referring to FIG. 1 in combination with FIGS. 2 to 5, there is shown a surgical stapling and cutting instrument, in particular, a linear surgical stapler 20 which is designed to staple and cut tissue. The linear surgical stapler 20 has a handle 21 at a first proximal end and an end effector 80 at an opposite distal end. The end effector 80 is curved in accordance with a preferred embodiment of the present invention. Right and left hand structural plates (often called "handle plates") 34, 35, respectively, connect the handle 21 to the end effector 80 of the instrument (the left hand handle plate is not shown in FIG. 1). The handle 21 has a right hand shroud 22 coupled to a left hand shroud (the left hand shroud is not shown in FIG. 1). The handle 21 also has a body portion 23 to grip and maneuver the linear surgical stapler 20 (see FIGS. 2 to 5).

The end effector 80 is a surgical fastening assembly that includes a cartridge module 120 (see FIGS. 6 to 9) and a C-shaped supporting structure 81. The term C-shaped is used throughout the specification to describe the concave nature of the supporting structure 81 and the cartridge module 120. The C-shaped construction facilitates enhanced functionality and the use of the term C-shaped in the present specification should be construed to include a variety of concave shapes which would similarly enhance the functionality of surgical stapling and cutting instruments. The distal end 30 of a closure member 28 is disposed to receive the cartridge module 120. The end effector 80 also includes a safety lockout mechanism 180 (best seen in FIG. 31) for preventing the firing of a previously fired cartridge module 120. The cartridge module 120 contains a cartridge housing 121 coupled to an anvil 122. The cartridge module 120 also includes a retaining pin 125, a knife 126, a removable retainer 160, a tissue contacting surface 127 which displays a plurality of staple-containing slots 128 in staggered formation in one or more rows (that is, staple lines) on either side of the knife 126. Staples (not shown) are fired from the cartridge housing 121 against staple-forming surface 129 of the anvil 122 that faces the tissue-contacting surface 127 of the cartridge housing 121.

As will become apparent based upon the following disclosure, the present linear surgical stapler 20 is designed as a multiple firing device with a replaceable cartridge module 120. However, it should be understood that many of the underlying concepts of the present invention may be equally applied in single firing devices without departing from the spirit of the present invention.

The supporting structure 81 of the end effector 80 is respectively attached to the right and left handle plates 34, 35, by a shoulder rivet 82 and posts 83 which extend from the supporting structure 81 into receiving holes in the handle plates 34, 35. In accordance with a preferred embodiment of the present invention, the supporting structure 81 is formed via a single piece construction. More specifically, the supporting structure 81 is formed by extrusion, for example, of aluminum, with subsequent machining to create the supporting structure 81 disclosed in accordance with the present invention. By constructing the supporting structure 81 in this manner, multiple parts are not required and the associated cost of manufacture and assembly is substantially reduced. In addition, it is believed the unitary structure of the supporting structure 81 enhances the overall stability of the present linear surgical stapler 20. In addition, the unitary extruded structure of the supporting structure 81 provides for a reduction in weight, easier sterilization since cobalt irradiation will effectively penetrate the extruded aluminum and less trauma to tissue based upon the smooth outer surface achieved via extrusion.

The handle 21 of the linear surgical stapler 20 includes a hand grip 24 which the surgeon grasps with the palm of his hand (see FIGS. 2–5). The hand grip 24 is composed of a right hand shroud handle 25 (see FIG. 1) and a left hand shroud handle (the left hand shroud handle is not shown in FIG. 1). Pivotally extending from the underside of the handle 21 are a closure trigger 26 and a firing trigger 27. The linear surgical stapler 20 illustrated in FIG. 1 is shown with the closure and firing triggers 26, 27 in their unactuated positions and with a cartridge module 120 inserted and the retainer 160 removed. Consequently, the cartridge housing 121 is spaced from the anvil 122 for the placement of tissue between the cartridge housing 121 and the anvil 122.

The handle 21 of the linear surgical stapler 20 contains a tissue retaining pin actuation mechanism 100. The tissue retaining pin actuation mechanism 100 includes a saddle shaped slide 101 positioned on the top surface of the handle 21. Manual movement of the slide 101 results in distal movement of the push rod 102. The push rod 102 is coupled to the retaining pin 125 of the cartridge module 120. The distal movement or proximal retraction of the push rod 102 results in corresponding movement of the retaining pin 125. The retaining pin actuation mechanism 100 is also releasably coupled to the closure trigger 26 within the handle 21 such that actuation of the closure trigger 26 will result in automatic distal movement of the retaining pin 125 if it has not already been manually moved to its most proximal position.

Figure 2:
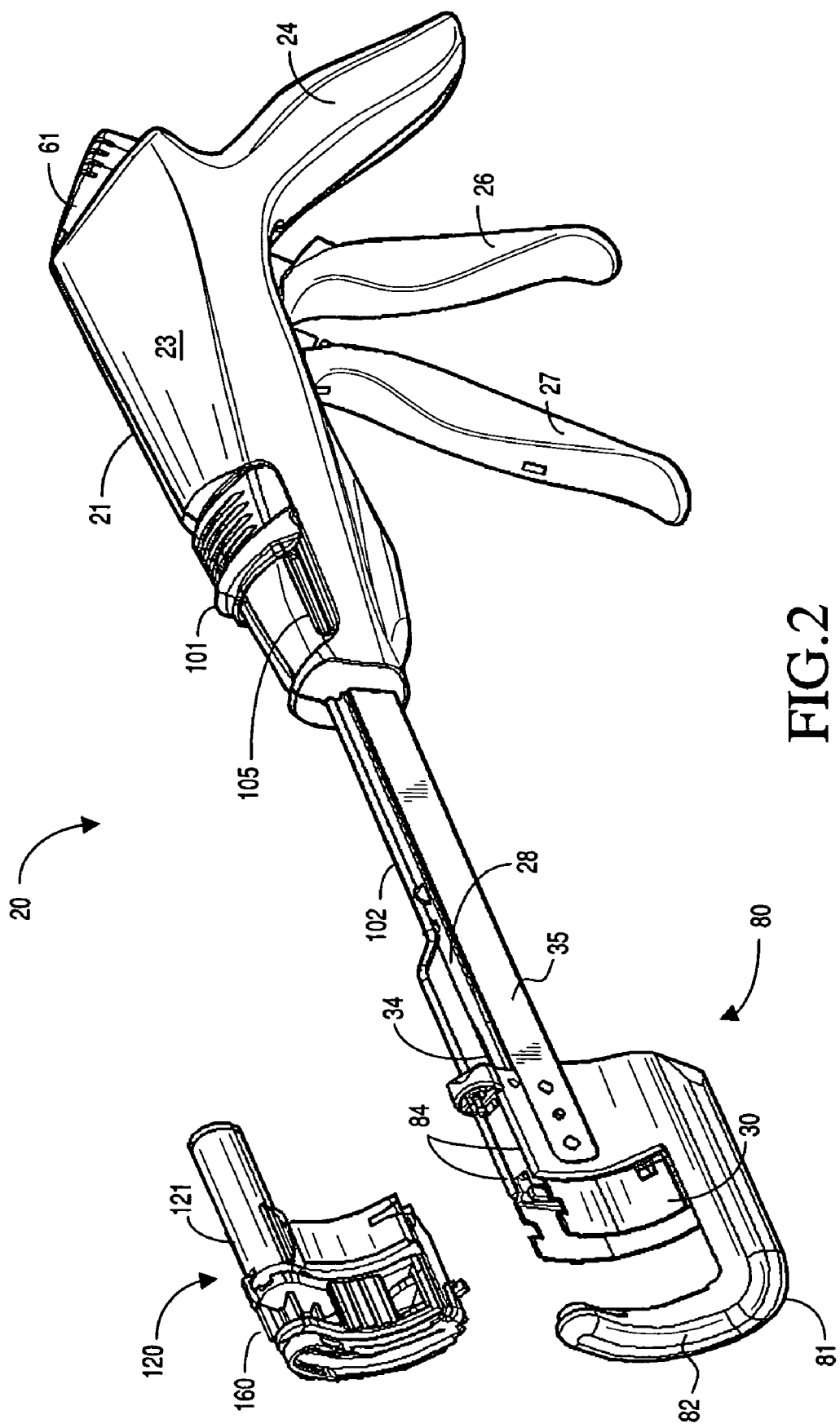
FIG. 2 is perspective view of the linear surgical stapler with the cartridge module removed.

Referring briefly to FIGS. 2 to 5, there is illustrated what happens when the cartridge module 120 is loaded and the closure and firing triggers 26, 27 are sequentially squeezed toward the hand grip 24 to actuate the end effector 80 of the linear surgical stapler 20. The linear surgical staple 120 is loaded with the cartridge module 120, as shown in FIG. 2, and the retainer 160 is removed. The linear surgical stapler 20 is now ready to receive tissue as shown in FIG. 1.

Figure 3:
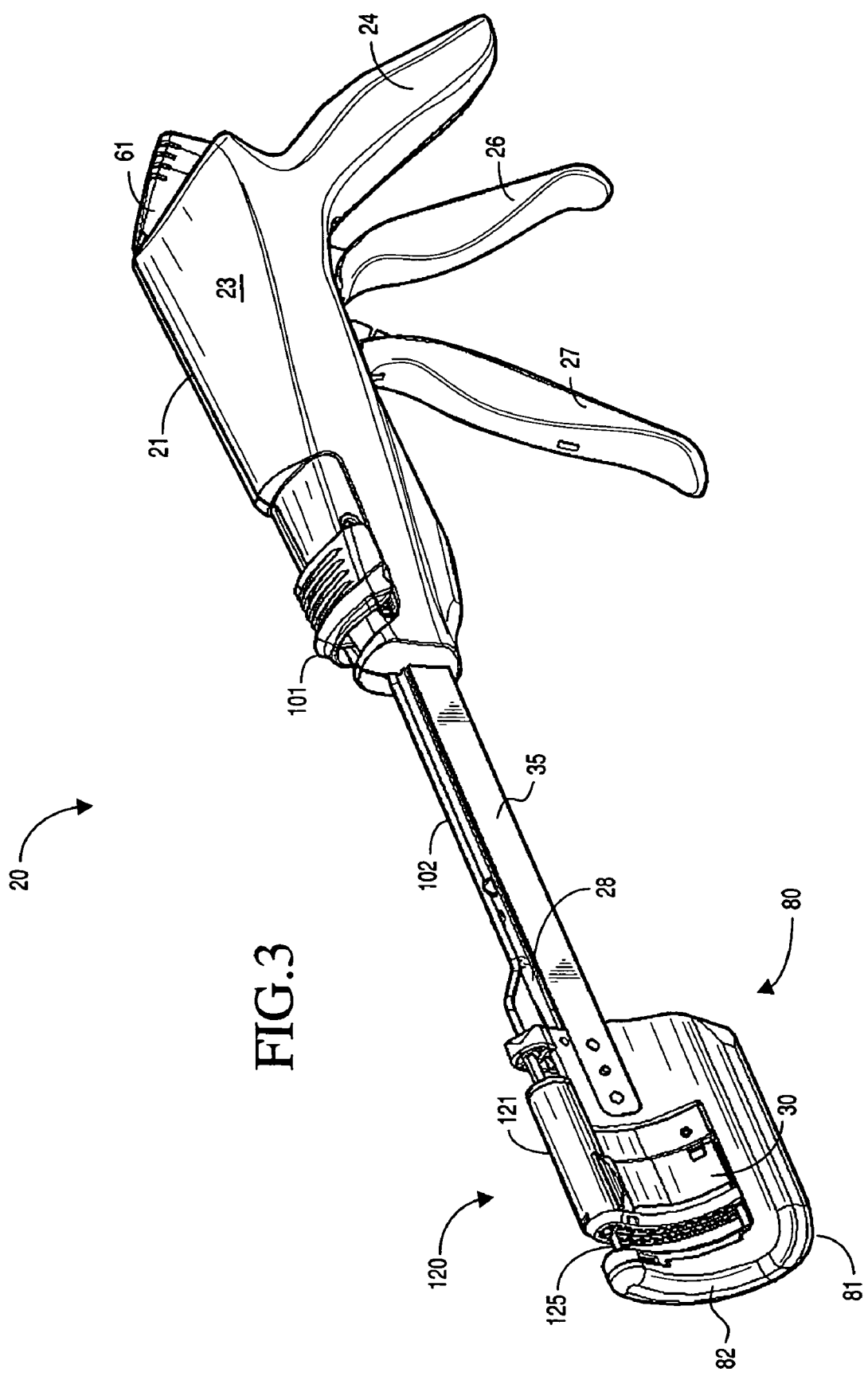
FIG. 3 is a perspective view of the linear surgical stapler with the cartridge housing moved to an intermediate position.

When the closure trigger 26 is partially squeezed to rest in its first detent position shown in FIG. 3, the cartridge housing 121 moves from its fully opened position to an intermediate position between the open and closed positions as discussed below in greater detail. Simultaneously, the tissue retaining pin actuation mechanism 100 moves the retaining pin 125 forward from the cartridge housing 121 through an opening in the anvil 122. In this position, tissue which has been placed between the cartridge housing 121 and the anvil 122 can be properly positioned, and the retention of the tissue between the cartridge housing 121 and the anvil 122 is assured. Therefore, when the closure trigger 26 has been actuated to its intermediate position, the cartridge housing 121 and anvil 122 are correspondingly positioned in their tissue retaining positions.

Figure 4:
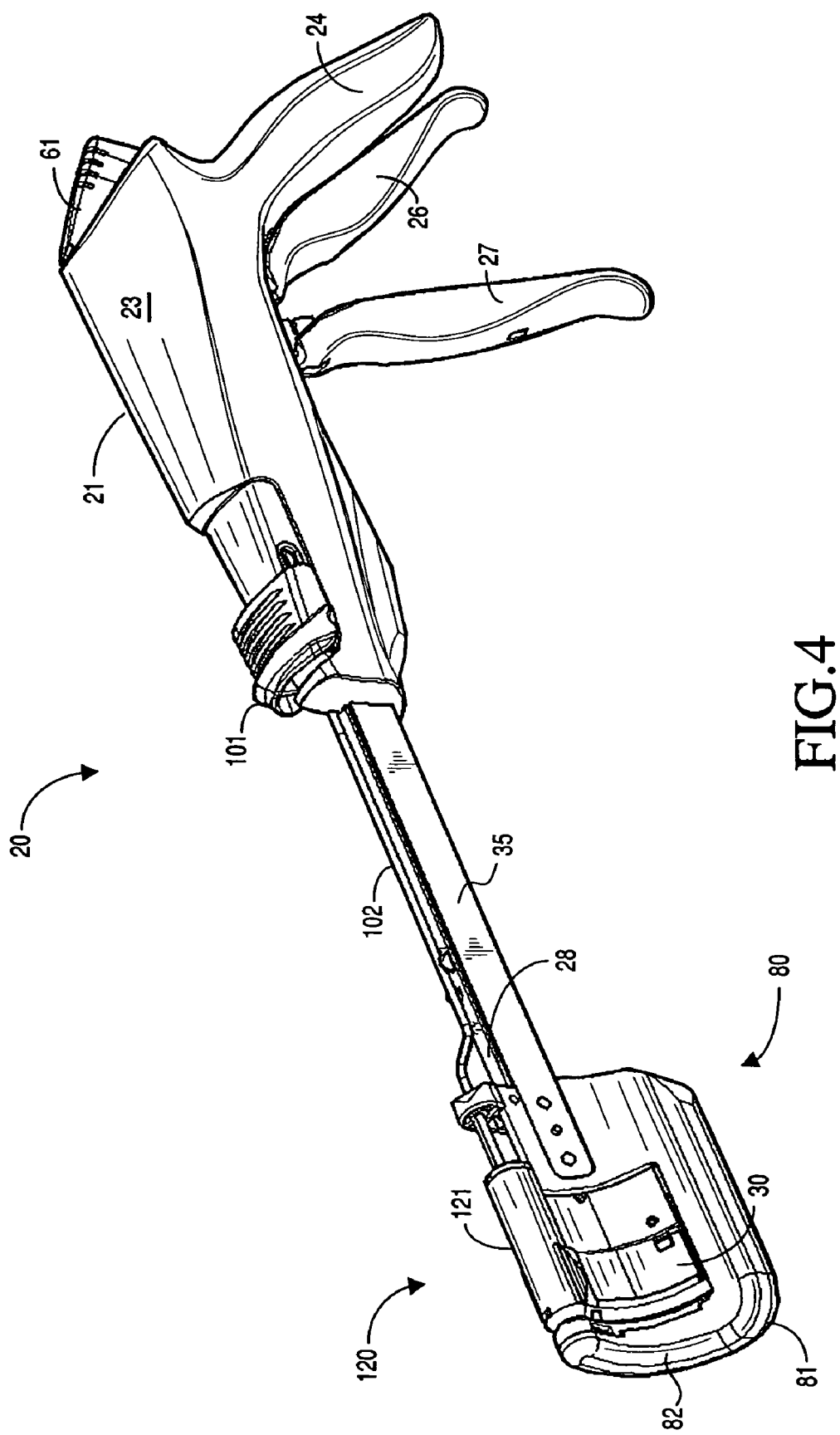
FIG. 4 is a perspective view of the linear surgical stapler with the cartridge housing moved to a closed position.
Figure 5:
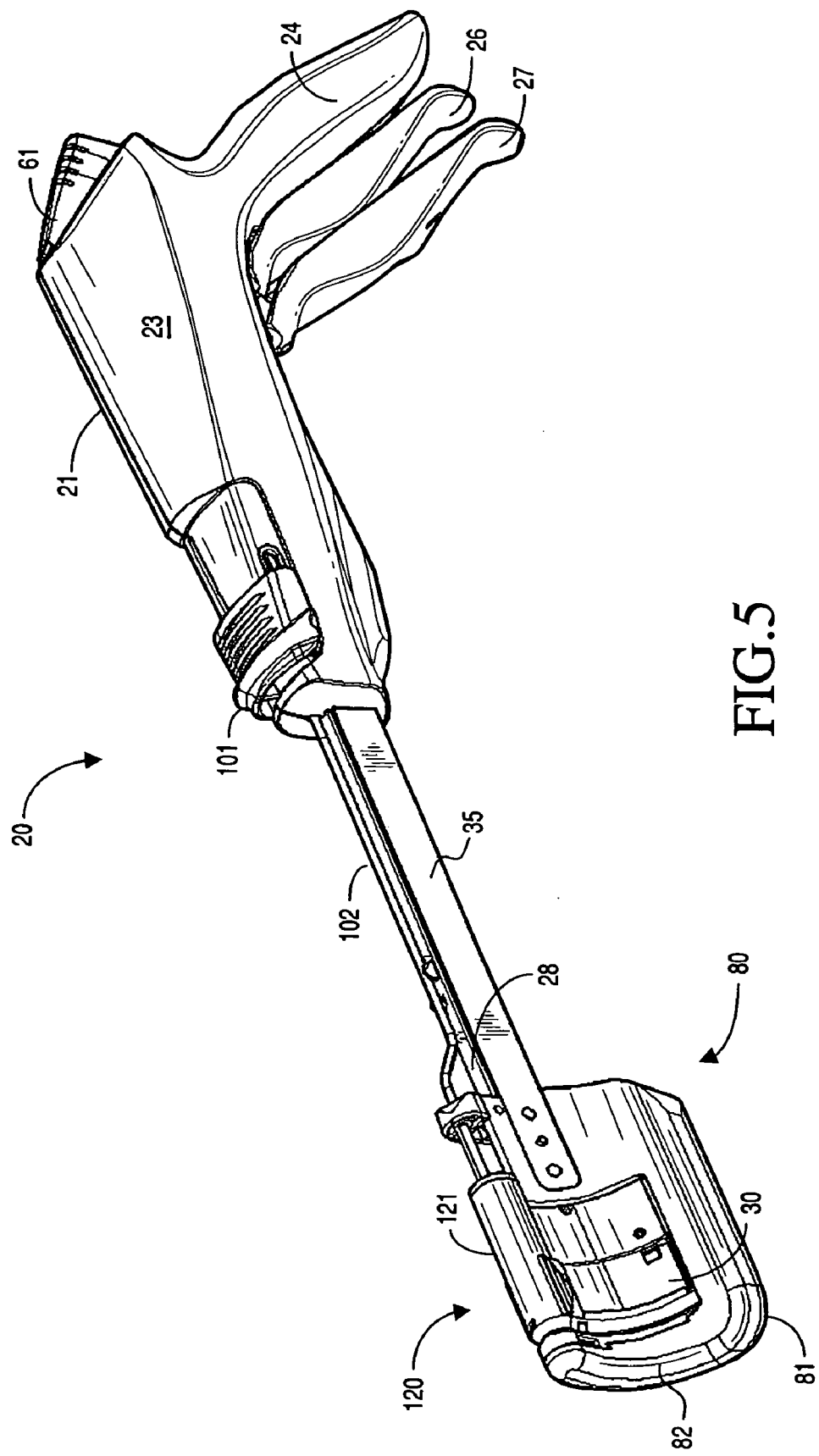
FIG. 5 is a perspective view of the linear surgical stapler with the firing trigger in a firing position.
Figure 6:
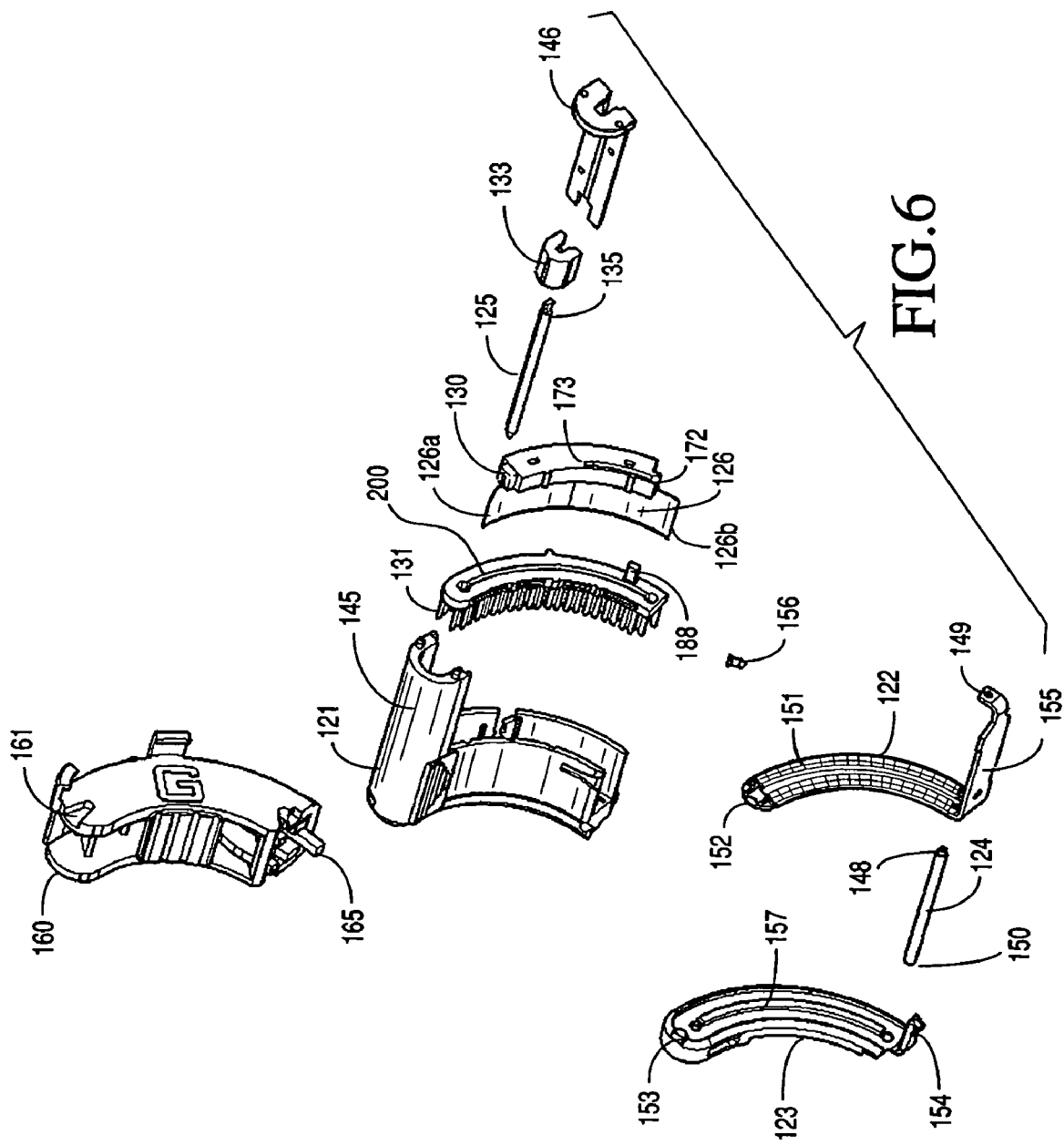
FIG. 6 is an exploded view of the cartridge module.

When the closure trigger 26 is fully squeezed so that it is adjacent the forward end of the hand grip 24, as illustrated in FIG. 4, the tissue contacting surface 127 of the cartridge housing 121 and the staple-forming surface 129 of the anvil 122 are adjacent to each other, and the properly positioned and retained tissue is consequently fully clamped. Additionally, the firing trigger 27 has rotated counterclockwise toward the handgrip 24 to enable the surgeon to grasp the firing trigger 27 for the firing of staples. Accordingly, the firing trigger 27 is now in position for the surgeon to squeeze it to staple and cut the tissue. When the firing trigger 27 has been fully squeezed to fire the staples, as shown in FIG. 5, the firing trigger 27 rests in near proximity to the closure trigger 26.

Referring now to FIGS. 6 to 9, a more detailed description of the cartridge module 120 is presented. The present cartridge module 120 provides a cutting and sealing mechanism for utilization within the linear surgical stapler 20 wherein the stapling and cutting functions operate in the same direction during device actuation. Although the present cartridge module 120 is particularly adapted for use in conjunction with linear surgical stapling devices, the concepts of the present cartridge module 120 may be applied to other surgical devices without departing from the spirit of the present invention. In particular, the present cartridge module 120 provides that the knife 126 be utilized in conjunction with a corresponding washer 123 during the cutting process. The present cartridge module 120 ensures that multiple firings of the linear surgical stapler 20 will not compromising cutting performance. This is accomplished by incorporating the anvil 122, in particular, the cutting washing 123, with the cartridge module 120. By combining the washer 123 with the cartridge module 120, a new washer 123 is provided each time the cartridge module 120 is replaced, resulting in improved cutting performance.

Enhanced performance is further provided by positioning the anvil 122 and the cartridge housing 121 parallel such that they move relative to each other with the facing surfaces of the anvil 122 and the cartridge housing 121 maintained in a parallel orientation. This provides for an even distribution of pressure across the tissue, preventing squeezing of the tissue in a manner which might bunch the tissue and force portions of the tissue out of the desired spaced defined between the anvil 122 and the cartridge housing 121.

More specifically, he cartridge module 120 includes a cartridge housing 121 that contains a plurality of staples (not shown) positioned in staple-containing slots 128. Immediately behind the staples is disposed a driver 131 which is disposed to push the staples out of the staple slots 128. A knife holder 130 is disposed immediately proximal of the driver 131 in the cartridge housing 121. The knife holder 130 contains a slot 172 and ledge 173 for interaction with a knife retractor hook 45 (see FIG. 37) in a manner which will e discussed below in greater detail. The knife holder 130 is attached to the knife 126 that extends distally from the knife holder 130 through a slot 200 in the driver 131 and through a slot 199 in the cartridge housing 121. Although the knife is disclosed as being within the housing in accordance with a preferred embodiment of the present invention, other configurations may be employed without departing from the spirit of the present invention; for example, it is contemplated that the cartridge module could be constructed without a knife if specific applications so dictate.

The knife holder 130 has a detent post 138 that extends through a slot 137 in the cartridge housing 121. The knife holder detent post 138 is disposed to contact detent protrusion 139 of the cartridge slot 137 during the longitudinal travel of the knife 126 and the knife holder 130. Similarly, the driver 131 has a detent post 140 that is disposed to contact proximal and distal detent protrusions 141, 142, respectively, of the cartridge slot 137. The detent posts 138, 140 of the knife holder 130 and the driver 131 provide a mechanism for controlling movement of the knife holder 130 and the driver 131. That is, the interaction between the detent post 138 of the knife holder 130 interacts with detent protrusion 139 to control movement of the knife holder 130 between a prefired and a retracted position, while the interaction between the detent post 140 of the driver 131 interacts with the proximal and distal detent protrusions 141, 142 to control movement of the driver between a prefired and retracted position.

In addition, and further to the other functions described below, the control mechanism provided by the detent posts 138, 140 and the detent protrusions 139, 141, 142, maintains the knife holder 130 in a desired position and maintains the driver 131 in a desired position after firing. Before use, this mechanism prevents the driver 131 from moving so that staples aren't fired until the doctor desires. In addition, the present mechanism prevents knife 126 from falling out the backside of the cartridge housing 121.

In accordance with a preferred embodiment, the cartridge housing 121 includes two separate detents ports for the driver 131 and the knife holder 130. In particular, driver detent port 140 is integrally formed with the driver 131 and the knife detent port 138 is integrally formed with the knife holder 130. The driver detent port 140 and the knife holder detent port 138 are shaped and dimensioned to interface with first and second flexible fingers 167, 168 molded into the side of the cartridge housing 121.

The first and second fingers 167, 168 are oriented parallel to the longitudinal axis of the cartridge module 120. The first finger 167 is shaped and dimensioned to contact the knife detent post 138 of the knife holder 130 and the second finger 168 is shaped and dimensioned to contact the driver detent post 140 of the staple driver 131. Protrusions 139, 141, 142, as discussed above, are positioned along the edge of each of the first and second fingers 167, 168. The location of the respective protrusions 139, 141, 142 is determined by the desired position of the driver 131 or knife holder 130 during operation. The shape of the protrusions 139, 141, 142 and the thickness of the flexible fingers 167, 168 are determined by the desired retention forces.

The present cartridge module 120 offers a variety of advantages. For example, compliance of the flexible fingers makes multiple cycles possible without loss of detent force and detent force can be "tuned in" by modifying the protrusion surfaces or cross sections of the fingers. In addition the protrusion surfaces allow different extension and retraction detent forces. For example, the force to overcome the knife detent post 138 during firing can be made to be significantly higher than the force to retract the knife 126 past the same detent post.

It is also an advantage of the present cartridge module 120 that the independent detents posts 138, 140 for the knife holder 130 and driver 131 allow the driver 131 to be held in an extended "fired" position as the knife 126 is retracted and retained in the unfired position. Since the knife 126 must slide through the staple driver 131 as it retracts, the staple driver detent post 140 ensures that the friction with the knife 126 does not cause the driver 131 to retract with the knife 126. If the driver 131 were to retract, the spent cartridge lockout mechanism 180 would not engage, causing a possibly hazardous situation.

In addition, the positioning of the detents posts 138, 140 on the side of the cartridge housing 121 give a visual indication of the position of the driver 131 and knife holder 130 within the cartridge housing 121. It also provides access to the detents posts 138, 140 so that they may be deflected in order to reload the cartridge module 120.

The knife 126 and slots 199, 200 are positioned such that there is at least one row of staples on either side of the knife 126. In accordance with a preferred embodiment of the present invention, two rows of staple slots 128 (and two rows of staples) are provided on each side of the slot 199 of the cartridge housing 121.

The cartridge housing 121 contains two generally circular openings 143, 144 at either end of the knife slot 199. The general circular opening 143 at the base of the cartridge housing 121 is shaped and dimensioned for the passage of a guide pin 124 through the cartridge housing 121. The generally circular hole 144 at the top of the cartridge housing 121 is shaped and dimensioned for the passage of a retaining pin 125 through the cartridge housing 121. The staple slots 128 are arranged such that the staples laterally extend past the generally circular holes 143, 144.

In accordance with a preferred embodiment of the present invention, the anvil 122 includes a plastic washer 123 and a metallic staple-forming surface 129. The anvil 122 is disposed to contain staple-forming surface 129 in a matching configuration with the staples. The retaining pin 125 is connected to a coupler 133 by a circumferential slot 135 in the retaining pin 125 and a groove 134 in the coupler 133 (best seen in FIG. 14). The coupler 133 is disposed within an arm 145 of the cartridge housing 121 and is held into the arm 145 by an end cap 146.

Figure 7:
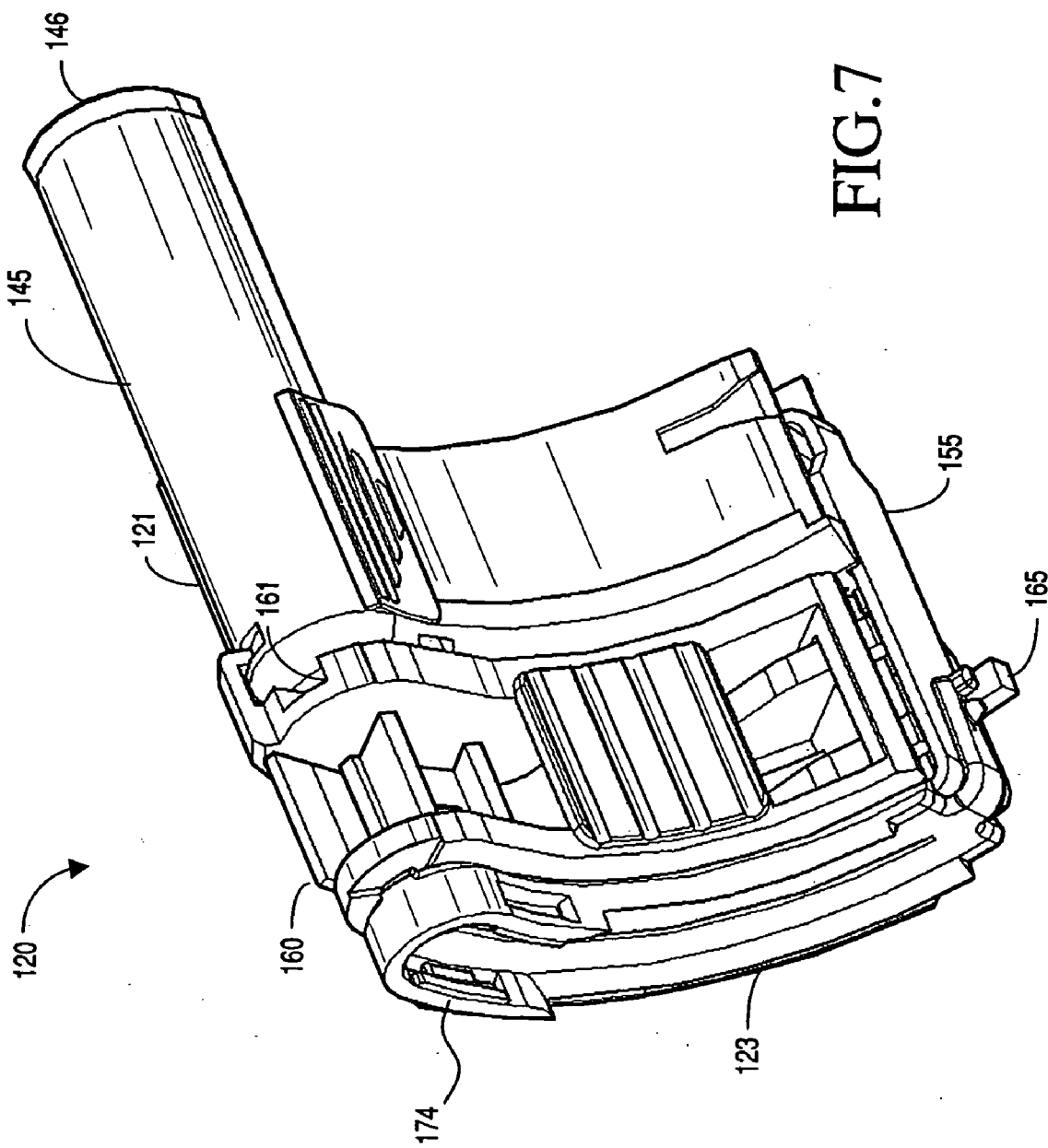
FIG. 7 is a front perspective view of the cartridge module with the retainer secured thereto.
Figure 8:
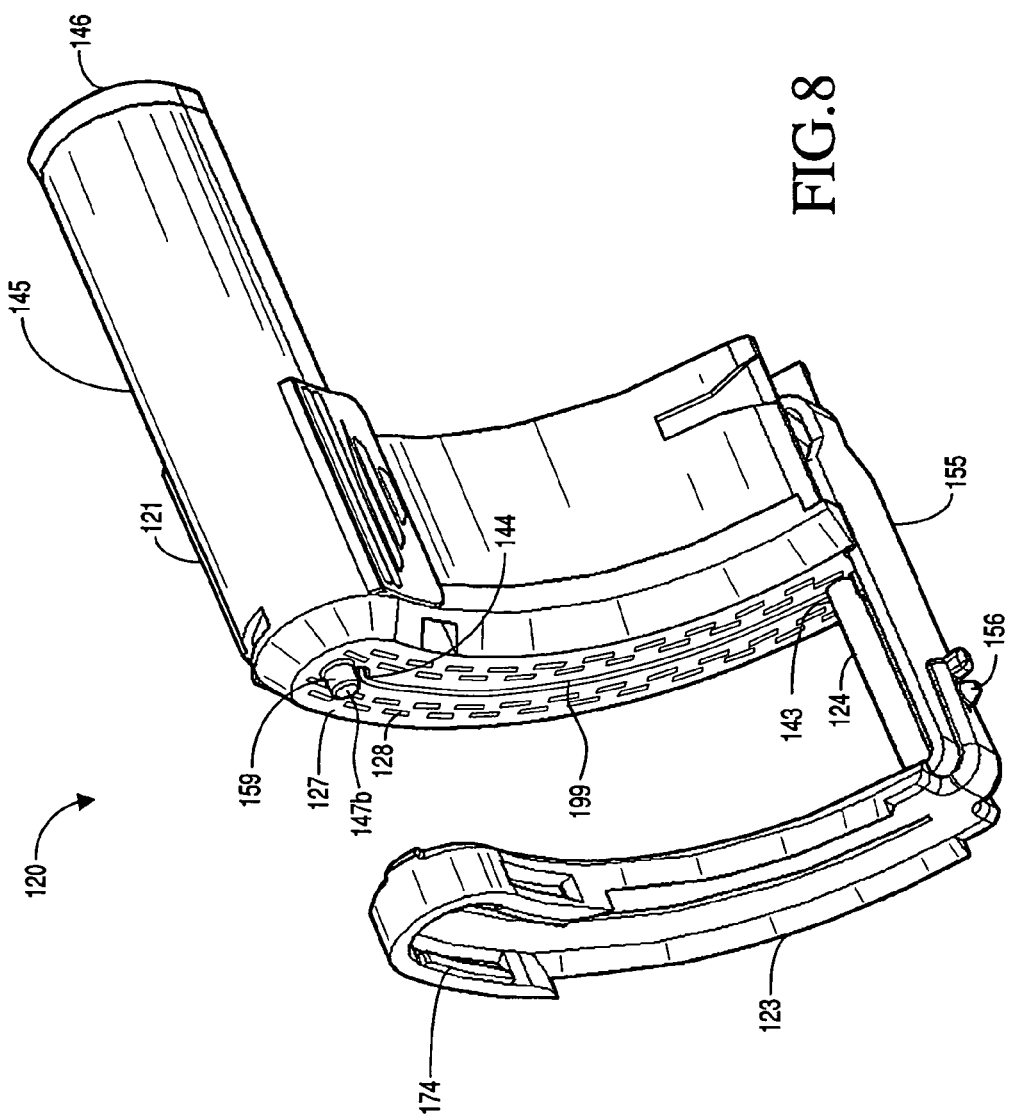
FIG. 8 is a front perspective view of the cartridge module with the retainer removed.

The guide pin 124 and retaining pin 125 include respective slots 147a, 147b (best seen in FIGS. 8, 9, 36, 39 and 40) into which the ends 126a, 126b of the knife 126 are disposed. The proximal end 148 of the guide pin 124 is connected to the proximal end 149 of the anvil 122. The distal end 150 of the guide pin 124 extends from the cartridge housing 121 and extends through a slot 151 of the anvil 122. A cutting washer 123 slips onto the anvil 122 by means of a groove 152 on the anvil 122 that fits under a tongue 153 on the washer 123. The opposite end 154 of the cutting washer 123 slips under the anvil arm 155 and is pinned to the anvil arm 155 by a pin 156. In this position, the cutting surface 157 of the washer 123 extends up through a slot 151 of the anvil 122. The assembly of the cutting washer 123 to the anvil 122 traps the guide pin 124 into the opening formed by the anvil slot 151 and the cutting surface 157, thereby, operatively connecting the anvil 122 to the cartridge housing 121. The retainer 160 is attached to the cartridge module 120 as shown in FIG. 7 to hold the components of the cartridge module 120 in a desired orientation until insertion into the end effector 80.

Turning to FIGS. 6 to 12 in combination with FIGS. 25 to 29, the retainer 160 will be described in more detail. The retainer 160 has a groove 161 that is disposed around a protrusion 159 of the cartridge housing 121. The retainer 160 contains a resilient inner spring arm 162 that is disposed for reciprocating movement within the retainer 160. The retainer 160 includes containment slots 163 which extend partially around the guide pin 124. The spring arm 162 includes containment slots 164 which extend partially around the guide pin 124, but are configured to face in an opposing direction to the containment slots 163. The retainer 160 is positioned onto the cartridge module 120 such that the containment slots 163, 164 surround the guide pin 124 and trap the retainer 160 onto the cartridge module 120. The spring arm 162 includes a disengagement tab 165 which extends down from the retainer 160 below the anvil arm 155. As such, the retainer 160 is not easily removed from the cartridge module 120 until the cartridge module 120 is properly seated within the end effector 80. Upon proper seating of the cartridge module 120 within the end effector 80, the disengagement tab 165 engages the end effector 80 for release of the retainer 160.

Figure 13:
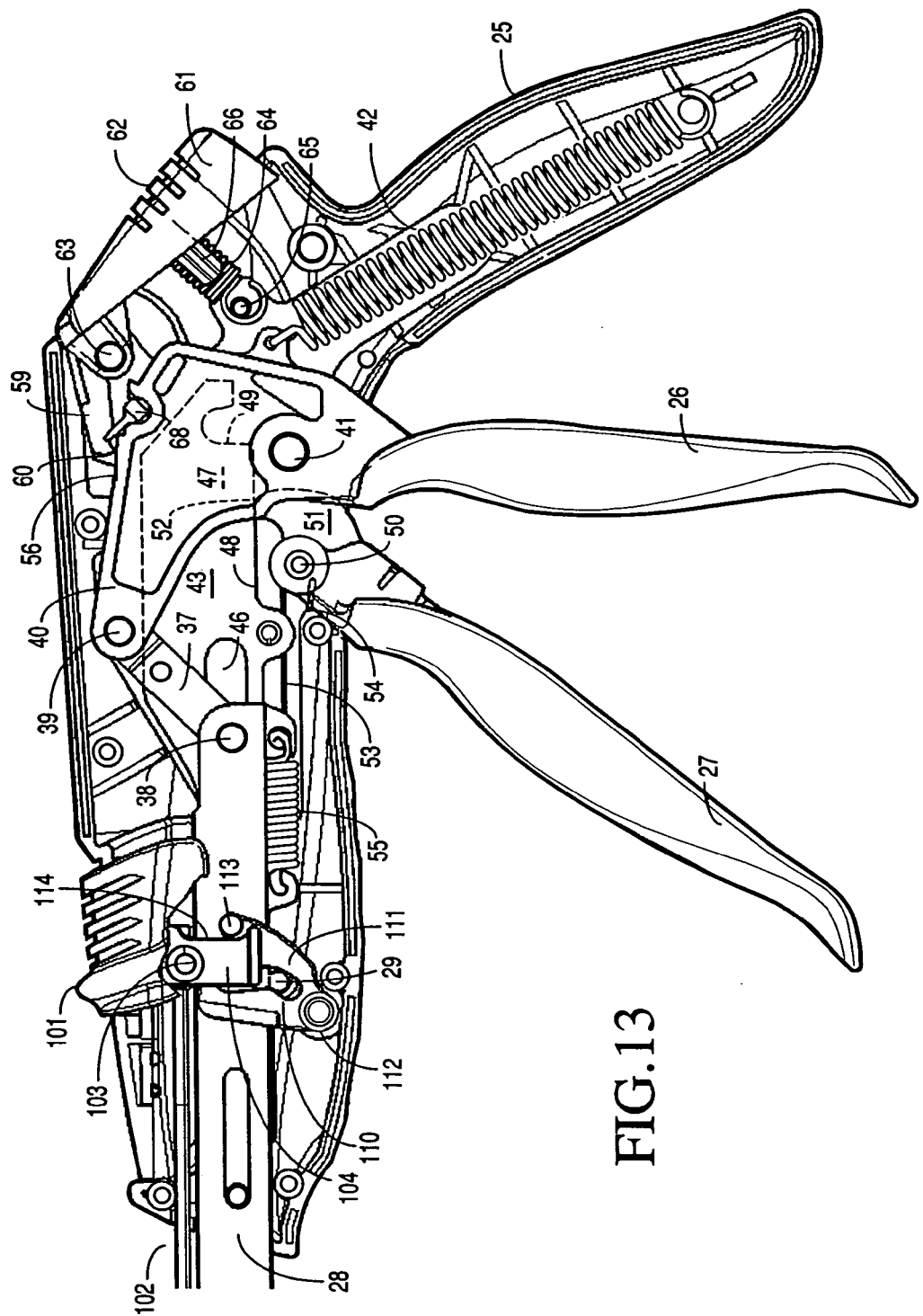
FIG. 13 is a partial cross-sectional view of the linear surgical stapler in an unactuated orientation.

Referring once again to FIG. 1 in combination with FIG. 2 and FIG. 13, a more detailed description of the components of the linear surgical stapler 20 is provided. The linear surgical stapler 20 includes an elongated closure member 28, with a generally C-shaped cross section, extending from the handle 21 into the surgical fastening assembly of the end effector 80. In accordance with a preferred embodiment of the present invention, the closure member 28 is a molded plastic member shaped for movement and functionality in accordance with the present invention. By manufacturing the closure member 28 from plastic, manufacturing costs are reduced and the weight of the linear surgical stapler 20 is also reduced. In addition, the linear surgical stapler 20 is easier to sterilize with cobalt irradiation as plastic is easier to penetrate than stainless steel. In accordance with an alternate embodiment, the closure member may be made from extruded aluminum with the final features machined into place. While an extruded aluminum closure member might not be as easy to manufacture as the plastic component, it would still have the same advantages (i.e., elimination of components, easier to assemble, lower weight, easier to sterilize).

The distal portion of the closure member 28 passes through the walls 84 of the supporting structure 81. The distal end is disposed to receive and retain the cartridge housing 121 of the cartridge module 120. The central portion of the closure member 28 is positioned between the right and left handle plates 34, 35, respectively. Right and left hand closure links 36, 37, respectively, are pivotally attached at the right and left proximal ends of the closure member 28 by a first integral closure link pin 38. At the opposite end of the closure links 36, 37, the closure links 36, 37 are pivotally attached to a second integral closure link pin 39. The second integral closure link pin 39 connects the closure links 36, 37 to a slotted closure arm link 40. The slotted closure arm link 40 is pivotally mounted to the handle plates 34, 35 of the linear surgical stapler 20 at a closure trigger pivot pin 41. The closure trigger 26 descends from the slotted closure arm link 40 for pivotal rotation about the closure trigger pivot pin 41 toward and away from the handgrip 24. A closure spring 42 housed within the hand grip 24 of the handle 21 is secured to the slotted closure arm link 40 to provide a desired resistance when the surgeon squeezes the closure trigger 26 toward the handle grip 24, and to bias the closure trigger 26 toward the open position.

Figure 14:
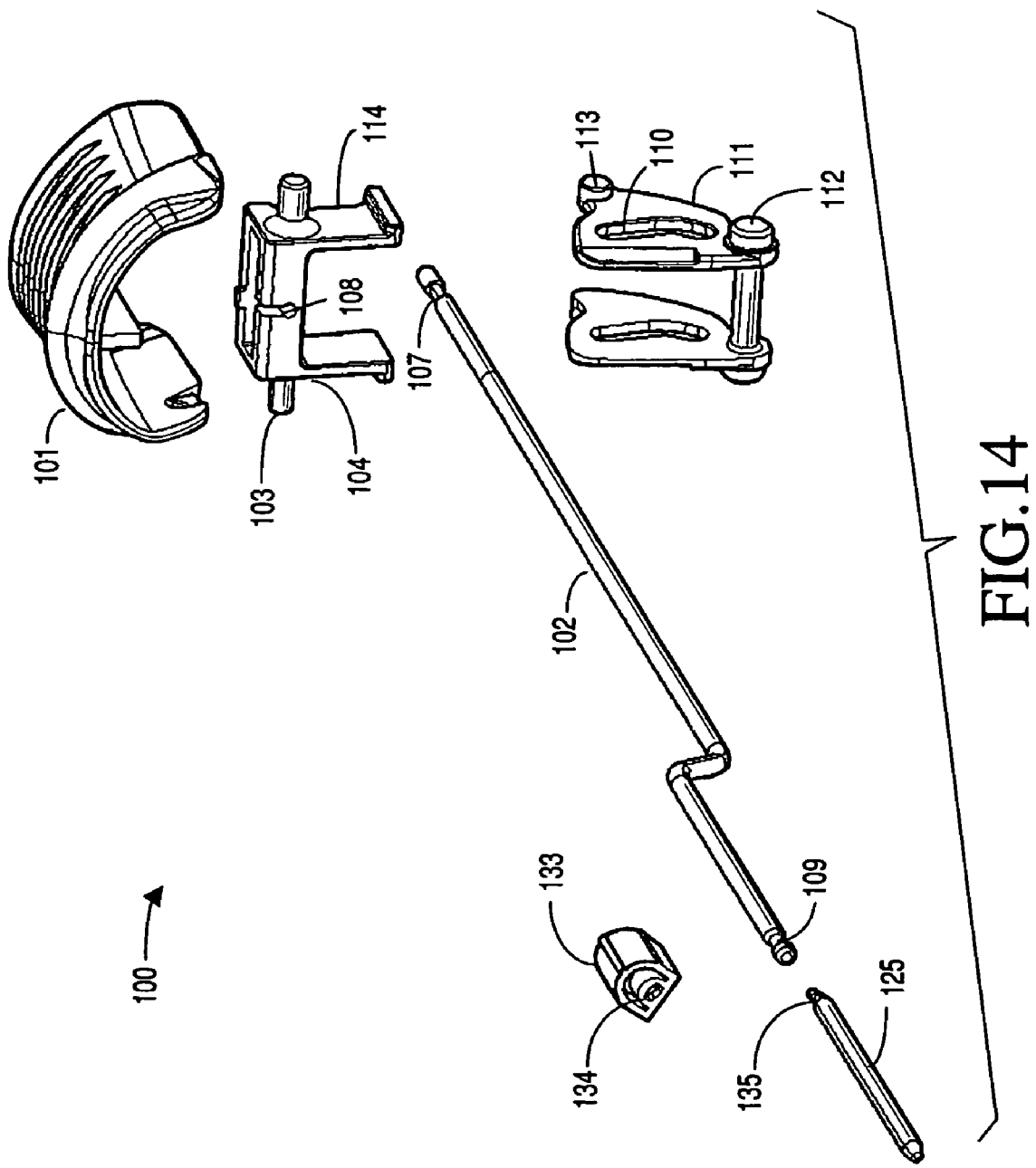
FIG. 14 is an exploded view of the pin actuation mechanism.
Figure 22:
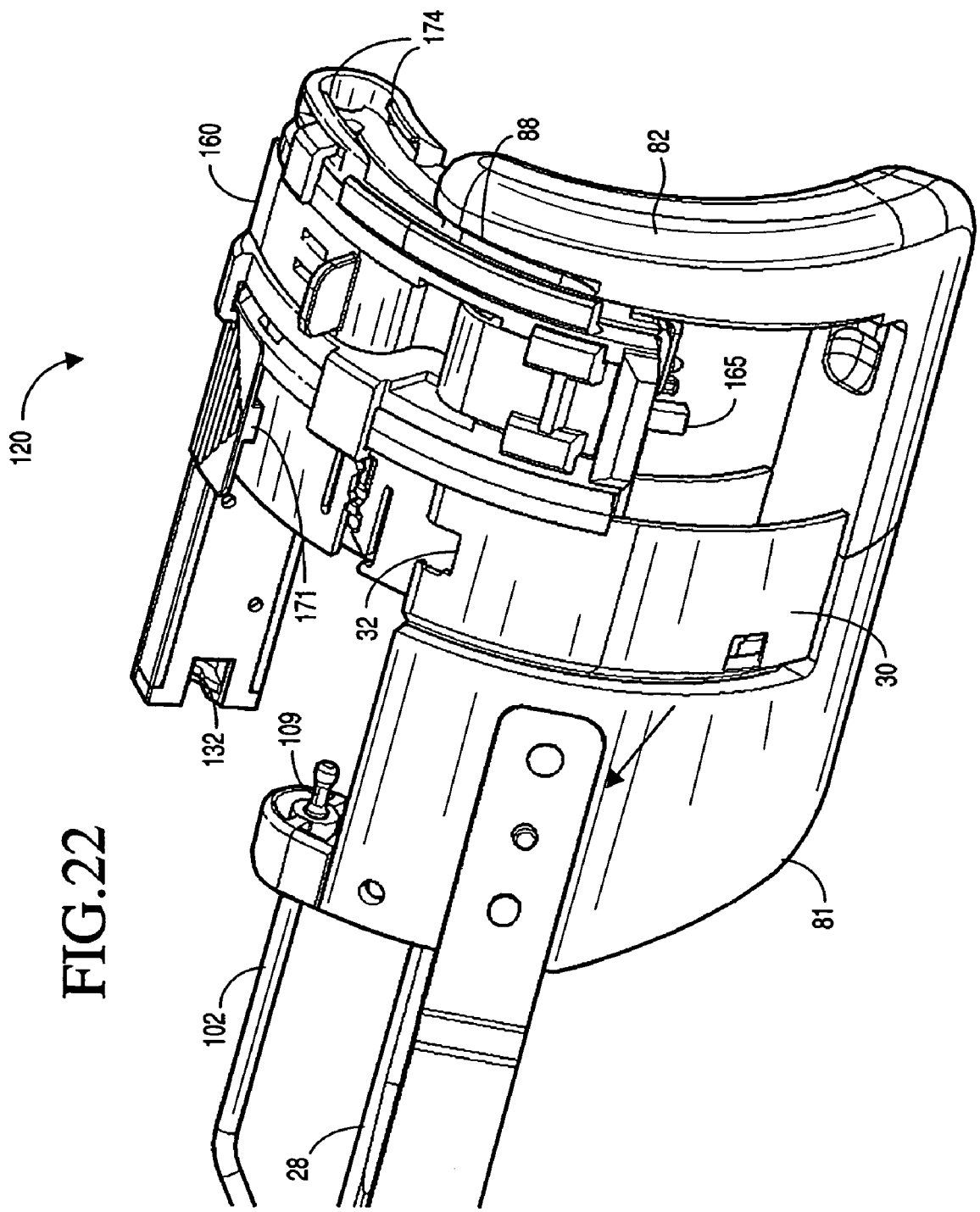
Figure 23:
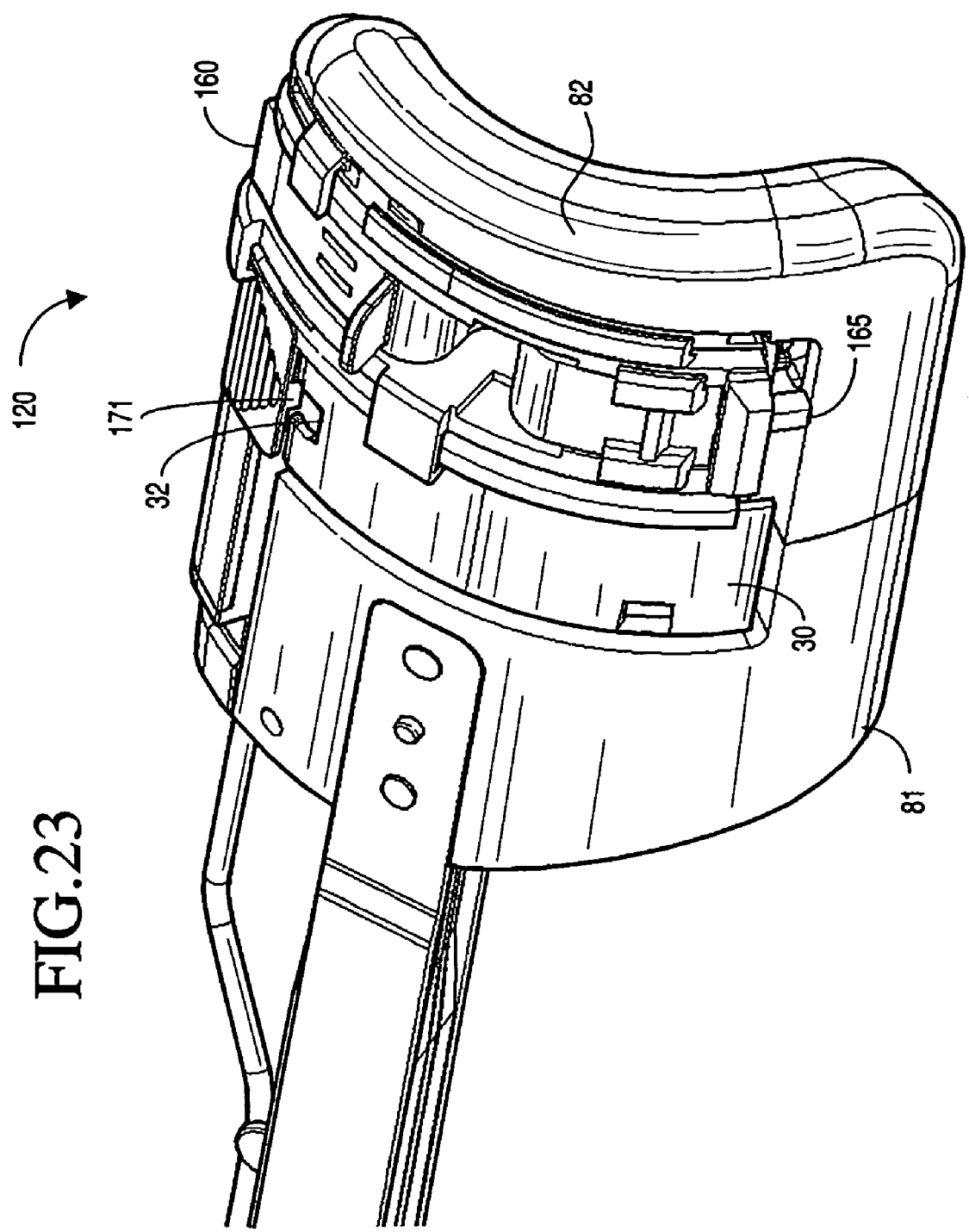

Referring to FIGS. 13 and 14, the components of the retaining pin actuation mechanism 100 will now be described. The handle 21 contains a saddle shaped slide 101 mounted on top of the handle 21 for linear motion. The slide 101 is connected to a post 103 that extends outward from a push rod driver 104 through slots 105 (see FIG. 2) in the handle 21. The push rod driver 104 is restrained for longitudinal movement along the long axis of the linear surgical stapler 20 by slots 105. The push rod driver 104 is connected to the push rod 102 by a circumferential groove 107 on the push rod 102 that snaps into a slot 108 of the push rod driver 104. The distal end of the push rod 102 contains a circumferential groove 109 that interconnects with a groove 132 in the proximal end of the coupler 133 of the cartridge module 120 (best seen in FIG. 22). The distal end of the coupler 133 contains a groove 134 for interconnecting with a circumferential slot 135 on the retaining pin 125.

The closure member 28 contains posts 29 which extend laterally on both sides of the closure member 28 inside the handle 21. These posts 29 slidably connect to an L-shaped slot 110 of a yoke 111. The yoke 111 is pivotally mounted to the handle 21 by a pivot pin 112 on the yoke 111. The yoke 111 contains cam pins 113 positioned to push camming surfaces 114 on the push rod driver 104.

Figure 37:
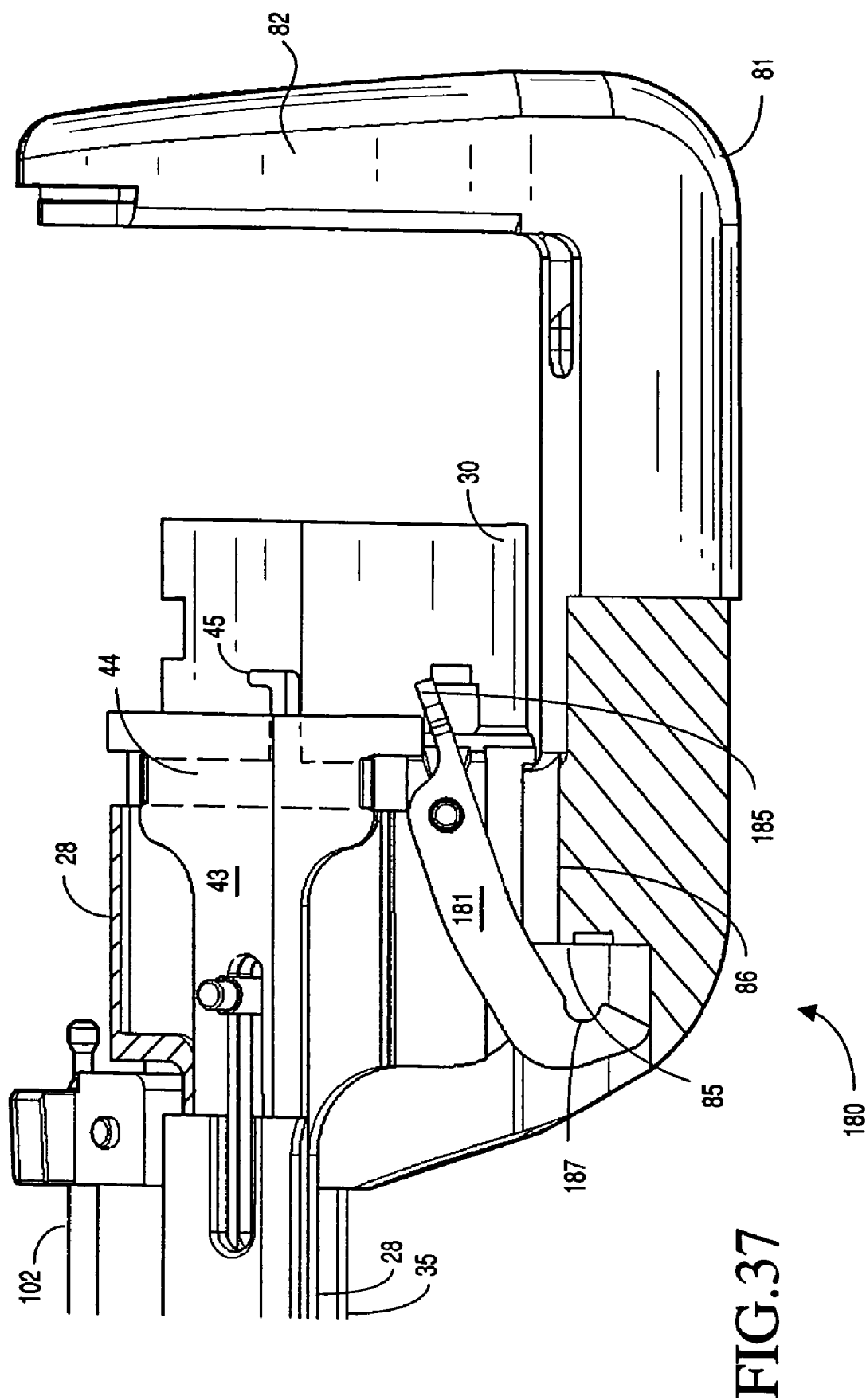

Referring to FIG. 13 and FIG. 37, the components of the firing transmission assembly will now be described. The firing transmission assembly has an elongated firing bar 43 extending from the handle 21 into the surgical fastening assembly of the end effector 80. The firing bar 43 is positioned within the C-shaped cross section of the closure member 28. The distal end of the firing bar 43 extends into the cartridge housing 121 and is positioned just proximally of the knife holder 130 and driver 131. The distal end of the firing bar 43 is attached to a knife retractor 44 that has a knife retraction hook 45.

The firing bar 43 has a rectangular receiving slot 46 in that portion of the ring bar 43 that is housed within the handle 21 (see FIG. 13). The first integral closure link pin 38 extends through the receiving slot 46. The firing bar 43 also has a proximal end section 47. The underside of the proximal end section 47 of the firing bar 43 has a sliding surface 48. The proximal end section 47 also has a terminal side engagement surface 49 extending from the sliding surface 48. The firing trigger 27 is pivotally mounted to the handle plates 34, 35 by a firing trigger pivot pin 50 spaced from the closure trigger pivot pin 41 so that each of the pivot pins pivot about mutually independent axes. The firing trigger 27 includes an arcuate firing trigger link 51 extending from the firing trigger 27 at the firing trigger pivot pin 50 to an apex 52 which rests on the sliding surface 48 of the proximal end section 47 of the firing bar 43. Within the handle 21, the firing trigger 27 is attached to first and second firing trigger spring arms 53, 54, respectively. The firing trigger spring arms 53, 54 support a torsion spring (not shown) on the right half of the firing trigger 43. Finally, a firing bar return spring 55 is secured to the underside of the firing bar 43 at that portion of the firing bar 43 within the handle 21 to bias the firing bar 43 toward its unactuated position.

When the closure trigger 26 is squeezed toward the handgrip 24, the slotted closure arm link 40 and the closure links 36, move distally within the receiving slot 46 of the firing bar 43. This distal movement causes the closure member 28 to correspondingly move distally. Likewise, the firing bar 43 concurrently moves distally with the closure member 28 because the first integral closure link pin 38, to which the closure links 36, 37 are attached, extends through the receiving slot 46 in the firing bar 43.

The mechanism which defines an intermediate closure detent position and the release of the closure trigger 26 from an actuated position to its original unactuated position will now be described in connection with FIG. 1 in combination with FIGS. 13–20. The top side of the slotted closure arm link 40 has a clamp sliding surface 56 that displays an intermediate detent 57 and a closure detent 58. A release pall 59 slides on the clamp sliding surface 56 and may engage the intermediate and closure detents 57, 58. The release pall 59 has a laterally extending pall lug 60 (best seen in FIG. 1) at its distal end. The release pall 59 is located within the handle 21, and it is integrally attached to a release button 61 situated exteriorly of the handle 21. The release button 61 has a thumb rest 62, and the release button 61 is pivotally attached to the handle 21 by a release trunnion 63. The release button 61 is biased outwardly from the handle 21 and, therefore, the release pall 59 is biased downwardly toward the clamp sliding surface 56 by a release spring 64 which is mounted to the handle 21 by a spring retention pin 65 and mounted to the release button 61 by a button spring post 66. The slotted closure arm link 40 has an arcuate recess 67 located between the intermediate and closure detents 57, 58. Sitting within this arcuate recess 67 for rotational movement are a left hand toggle 68 integrally connected to a right hand toggle (the tight hand toggle is not shown). Each toggle 68 has a toggle arm 69 that is engageable with the pall lug 60. The pall lug 60 has a concave proximal surface 70 to provide clearance between the toggle arm 69 and the pall lug 60.

Figure 31:
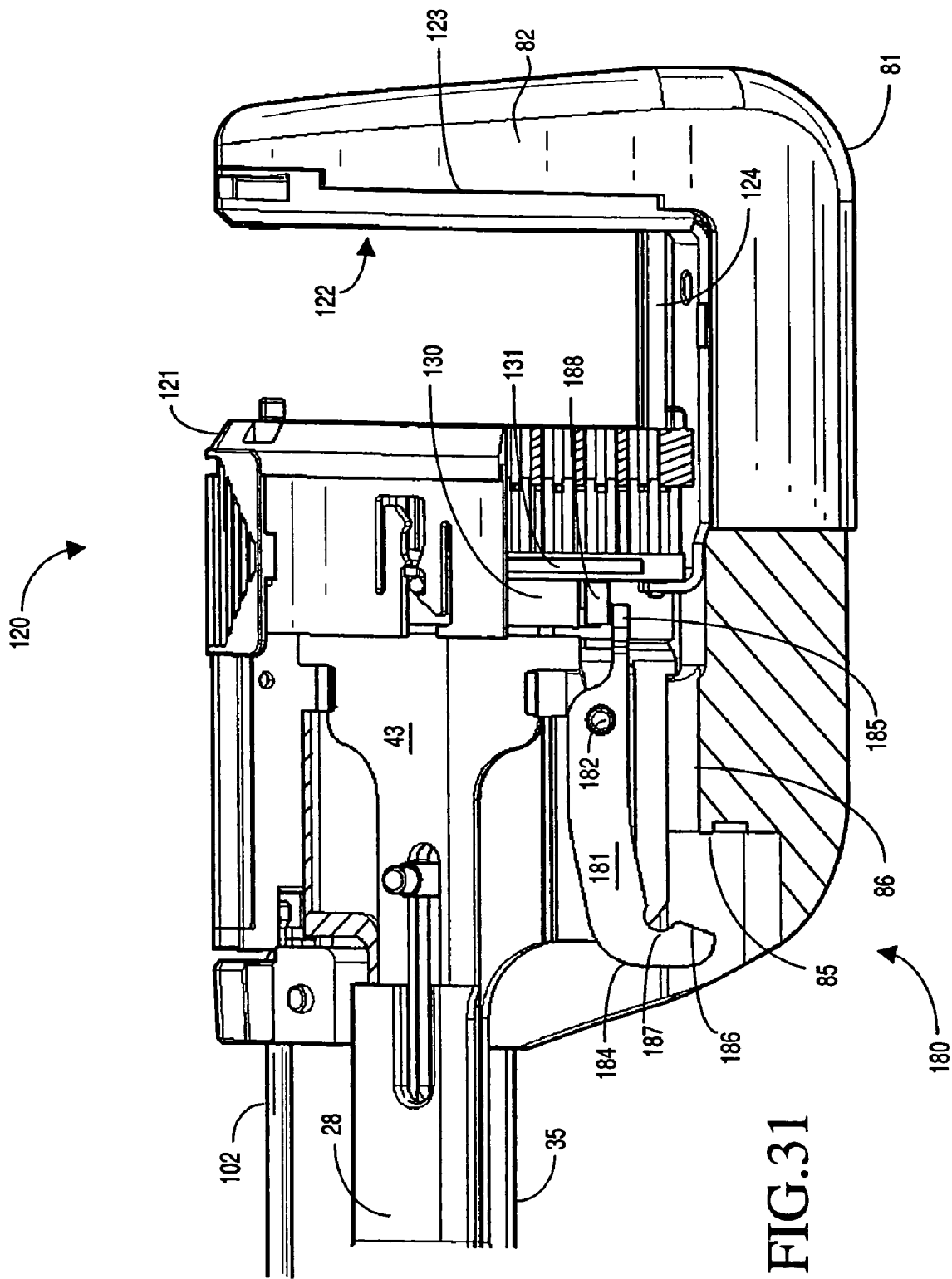

Referring to FIG. 31 (cut away view into cartridge and supporting structure), the components of the fired device lockout mechanism 180 will now be described.

As will be appreciated based upon the following disclosure, once the device has been fired the lockout mechanism 180 prevents movement of the cartridge housing 121 to its second closed position but permitting relative reapproximation movement of the cartridge housing 121 and anvil 122, whereby reapproximation provides an indicator that the instrument is not malfunctioning. Permitted reapproximation will constitute approximately ¼ to approximately ⅔ of the total distance between the cartridge housing 121 and the anvil 122 when in the first spaced apart position, and more preferably, ¼, ⅓, or ½ of the total distance between the cartridge housing and the anvil when in the first spaced apart position.

The lockout mechanism 180 contains a lockout lever 181 that is pivotally mounted to the distal end 30 of the closure member 28 by a pin 182. The lockout lever 181 is spring biased down toward the base of supporting structure 81 by a spring (not shown). The lockout lever 181 contains a proximal and distal end 184, 185, respectively. The proximal end 184 has a cam surface 186 and locking groove 187. The supporting structure 81 of the end effector 80 contains a ledge 85 that is disposed to interact with locking groove 187 when the lockout mechanism 180 is engaged. The supporting structure 81 contains a base surface 86 between walls 84. The base surface 86 is disposed to interact with cam surface 186 when the lockout lever 181 is not engaged.

The operation of loading the cartridge module 120, the closure mechanism, the retaining pin mechanism, the firing transmission assembly, the intermediate and closure detents 57, 58, the release mechanism, and the lockout mechanism 180 will now be described. Referring to FIGS. 7 to 12 and FIGS. 21 to 28 the loading of the cartridge module 120 into the tissue end effector 80 is described. The cartridge module 120 is shaped and dimensioned for selective insertion and removal from the tissue end effector 80 of the linear surgical stapler 20.

Figure 25:
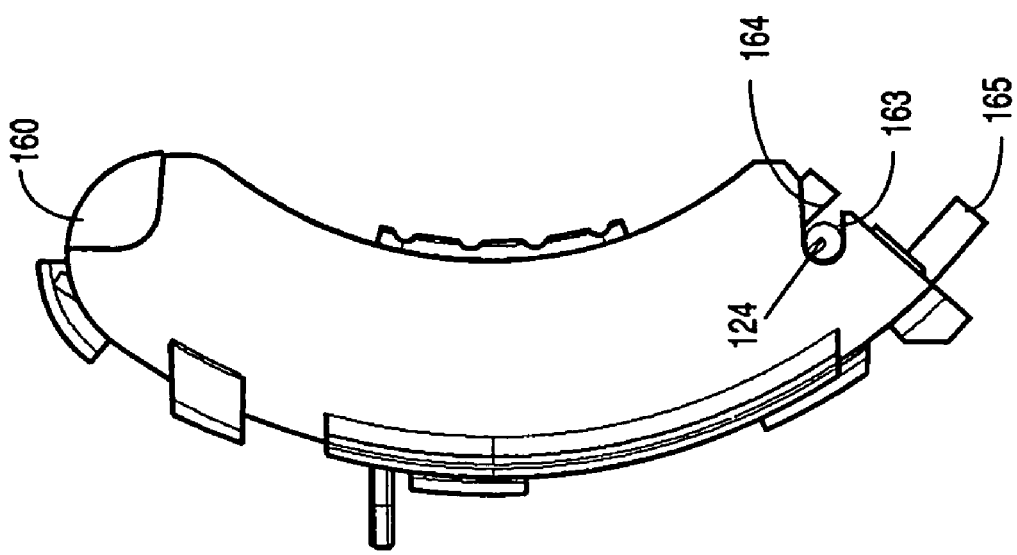

Prior to insertion of the cartridge module 120 into the end effector 80 of the linear surgical stapler 20, as seen in FIG. 7, the retainer 160 can not easily be removed from the cartridge module 120 as the groove 161 is disposed around the protrusion 159 at the top end of the retainer 160 preventing disconnection. Further, the containment slots 163, 164 of the retainer are disposed around the guide pin 124 at the bottom of the retainer 160 preventing disconnection as shown in FIG. 25. The attached retainer 160 provides support to the structure of the cartridge module 120 and an extended surface area for gripping, both features making loading easier. The retainer 160 also prevents staples from dislodging from the cartridge housing 121 during casual handling and prevents the knife 126 from accidental exposure during casual handling.

Figure 9:
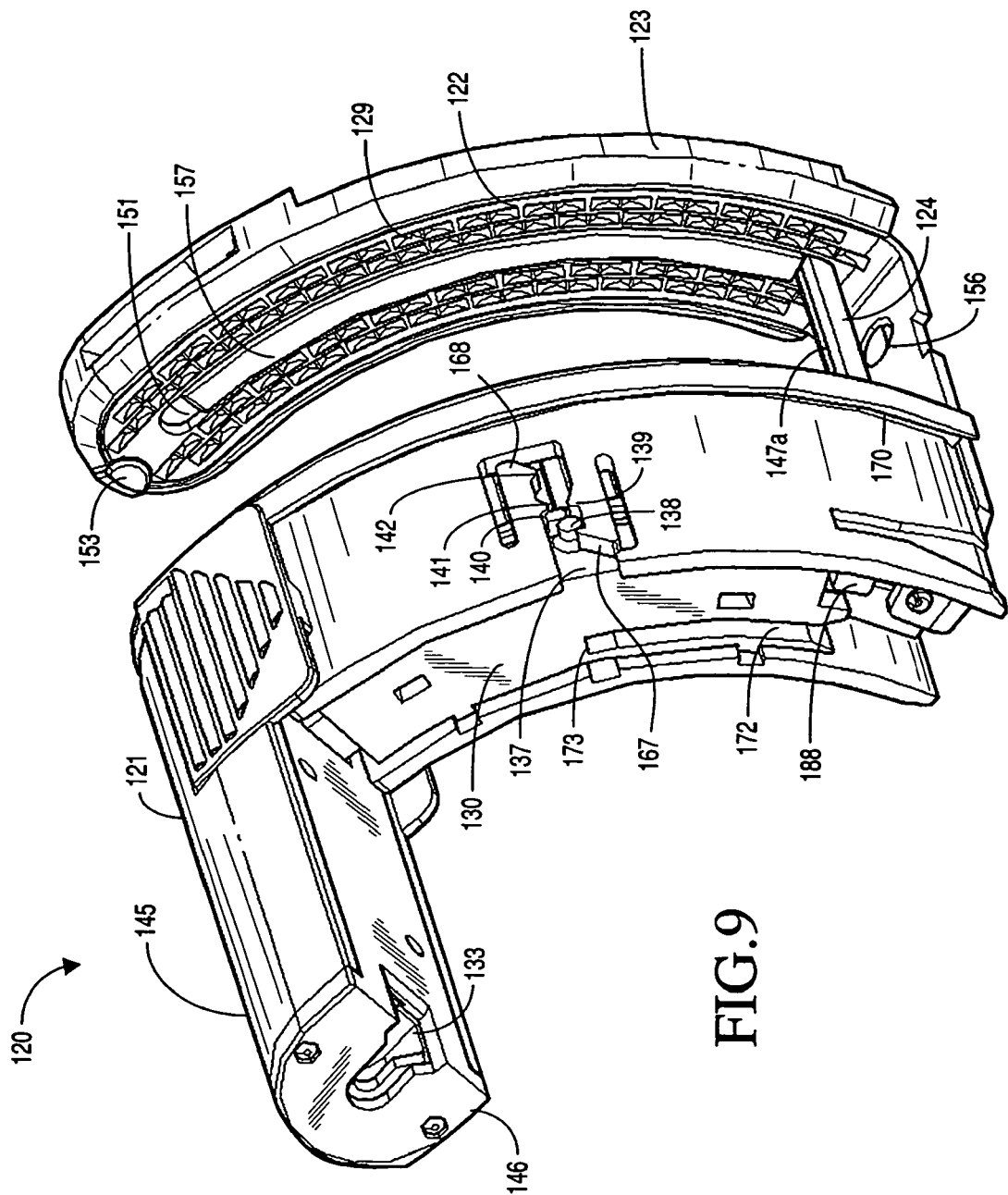
FIG. 9 is a rear perspective view of the cartridge module showing the cartridge housing slot in substantial detail.

Knife 126 movement and staple movement are further resisted prior to loading and during loading by a series of detents. Referring to FIG. 9, detent post 138 on the knife holder 130 is prevented from proximal and distal movement by the detent protrusion 139 on the cartridge housing slot 137. The driver 131 is prevented from distal movement due to casual handling and during loading of the cartridge module 120 into the linear surgical stapler 20 by the interaction of the detent post 140 and the detent protrusion 141 on the cartridge housing slot 137.

The cartridge module 120 is loaded into the tissue effector 80 such that the cartridge housing 121 slips into the distal end 30 of the closure member 28 as seen in FIGS. 21 to 24. Walls 31a and 31b on the closure member 28 slip into slots 170a, 170b of the cartridge housing 121 during loading. Simultaneously, tabs 174 (See FIG. 8) slip into groove 88 of the C-shaped supporting structure 81. Loading of the cartridge module 120 is completed when the detents 171 snap onto the detent groove 32 of the closure member distal end 30, as shown in FIGS. 21 to 24.

Figure 24:
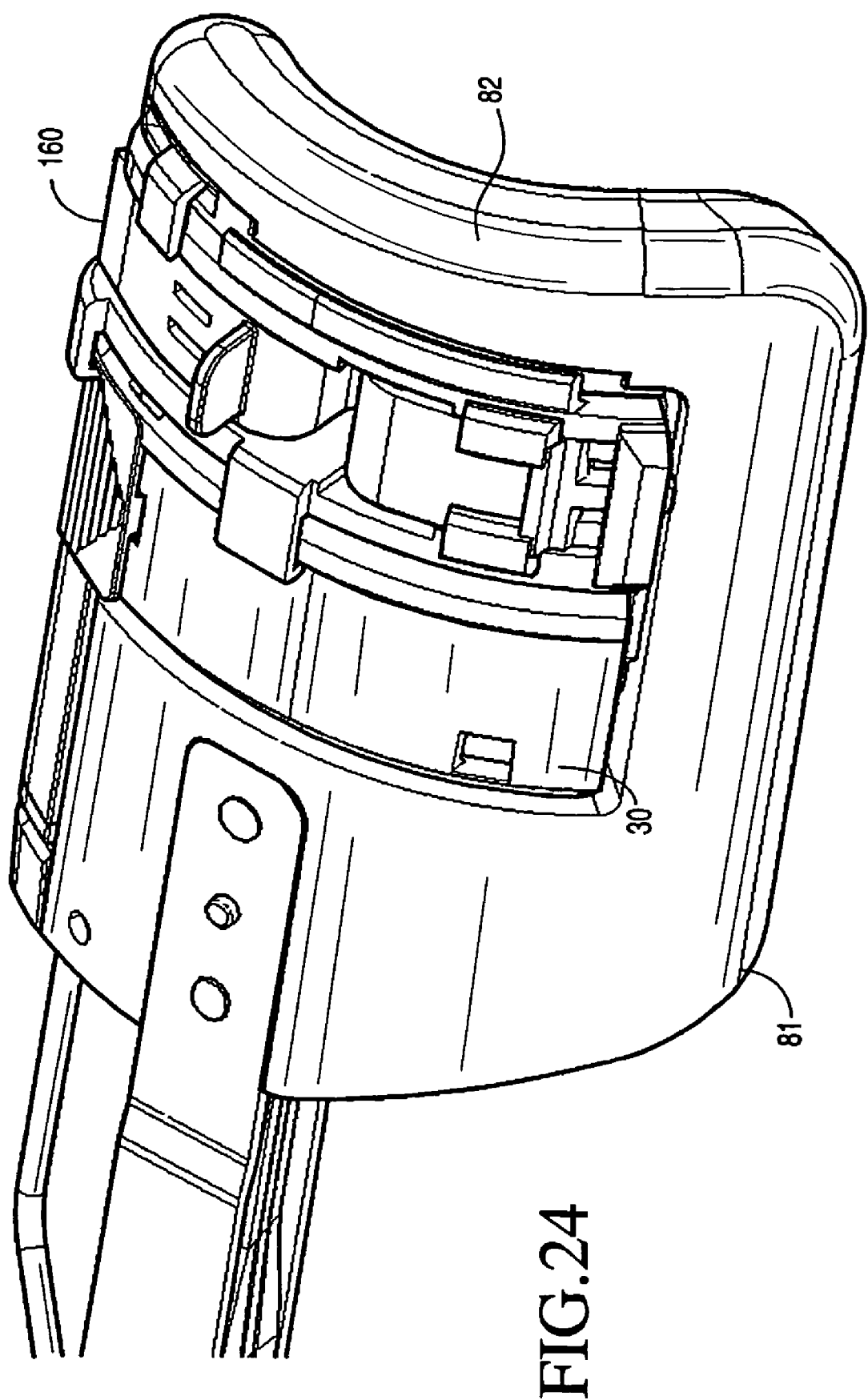
Figure 26:
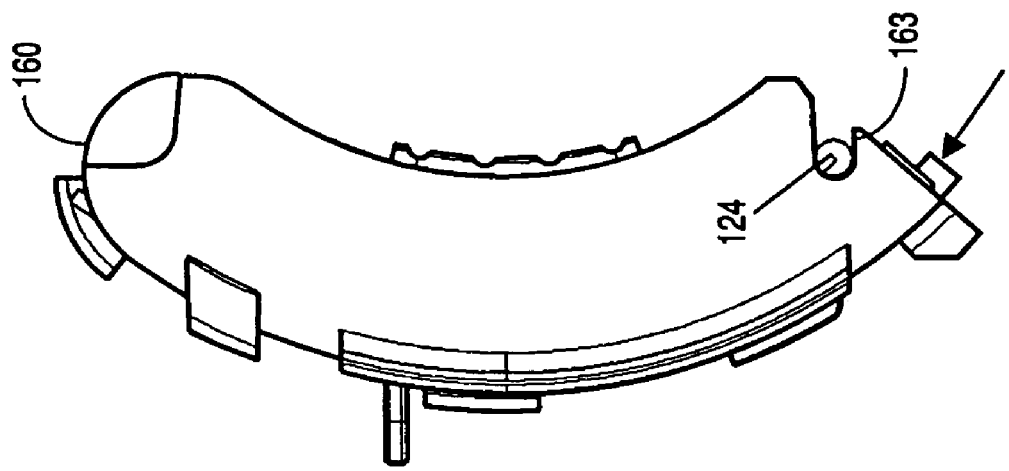

In the position shown in FIG. 24, the cartridge module 120 is fully loaded and the proximal groove 132 of the coupler 133 has engaged the distal circumferential groove 109 of the push rod 102 such that the retaining pin 125 in the cartridge module 120 has been connected to the retaining pin advancement mechanism 100. The slot 172 of knife holder 131 engages the knife retraction hook 45 during loading such that the hook 45 has engaged the retraction ledge 173 on the knife holder 130 at the completion of the cartridge module 120 loading.

At the completion of the cartridge module 120 loading a post 188 positioned on driver 131 contacts the distal end 185 of the lockout lever 181 (see FIG. 31). This contact pivots the lockout lever 181 about the lockout lever pin 182 to a position such that the camming surface 186 is horizontally aligned with the base surface 86 of the C-shaped supporting structure 81.

Figure 27:
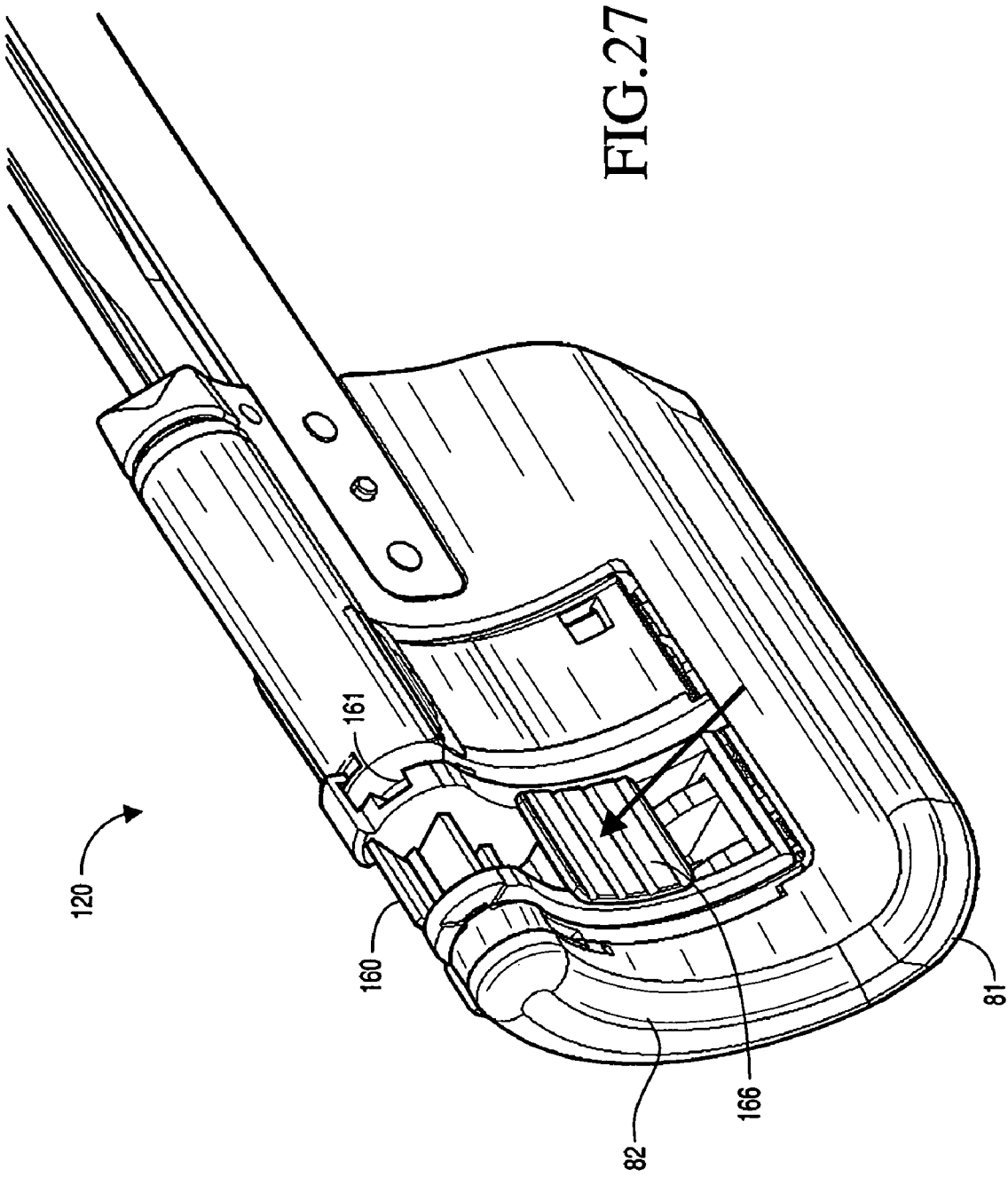
Figure 28:
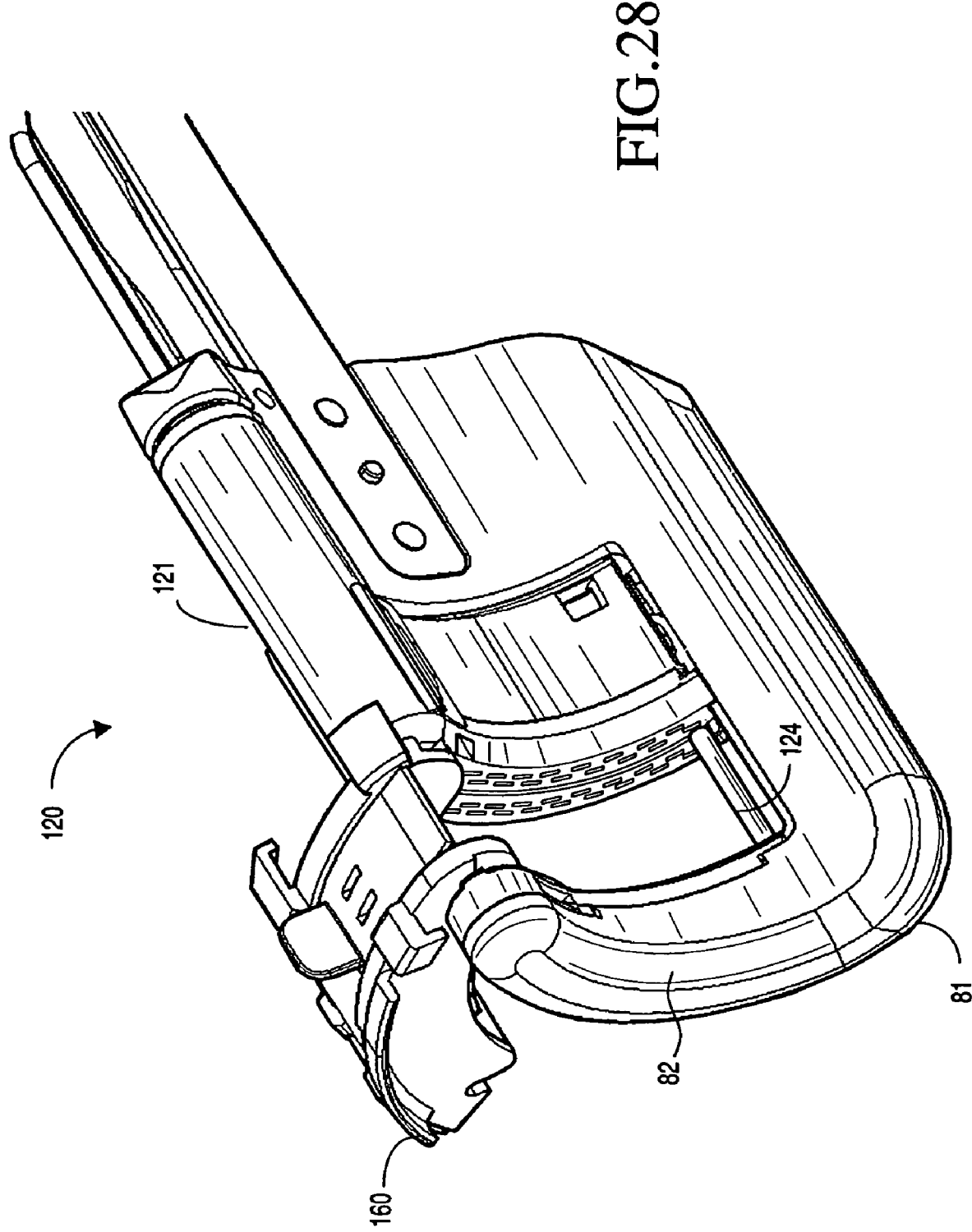
Figure 29:
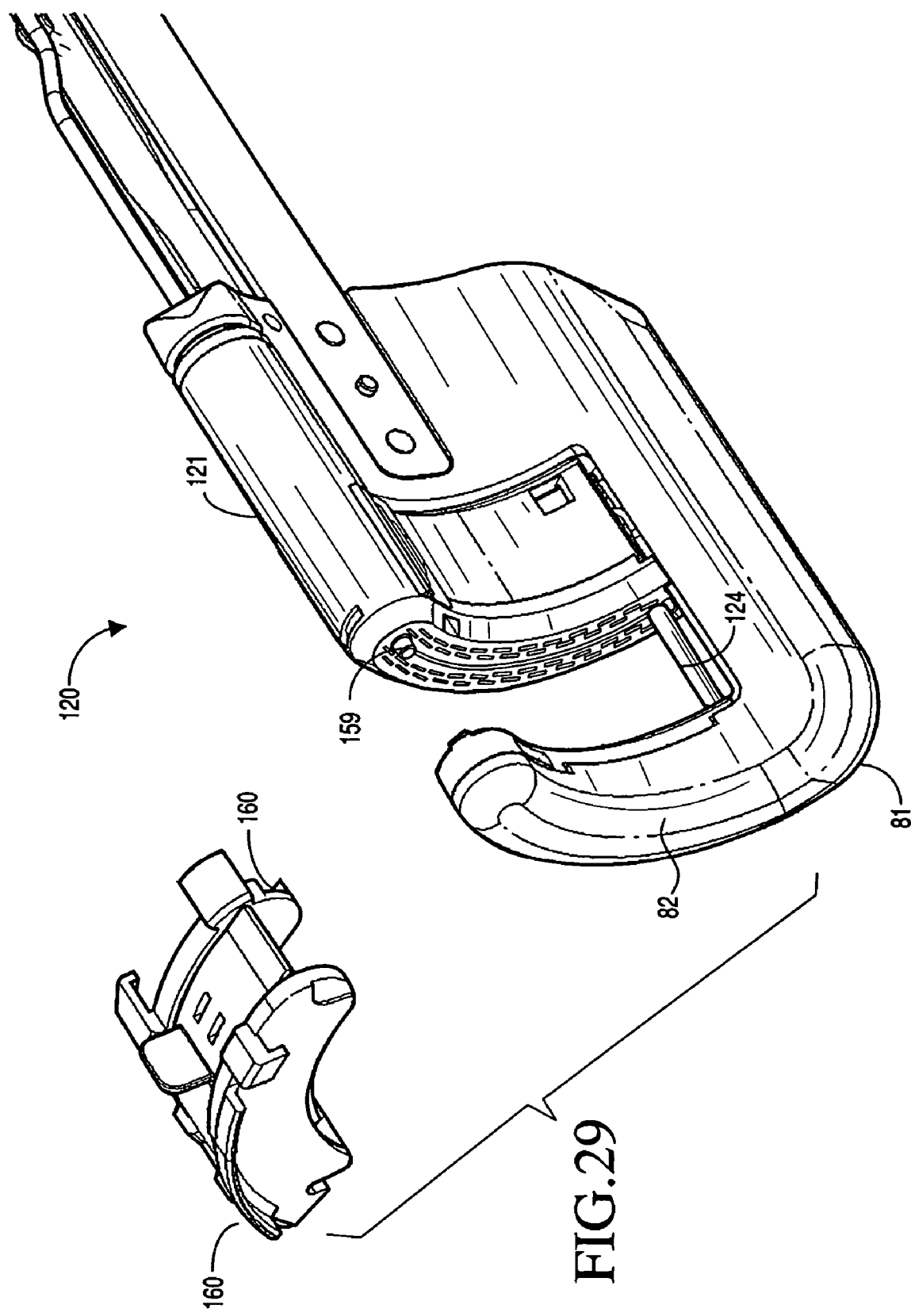
Figure 30:
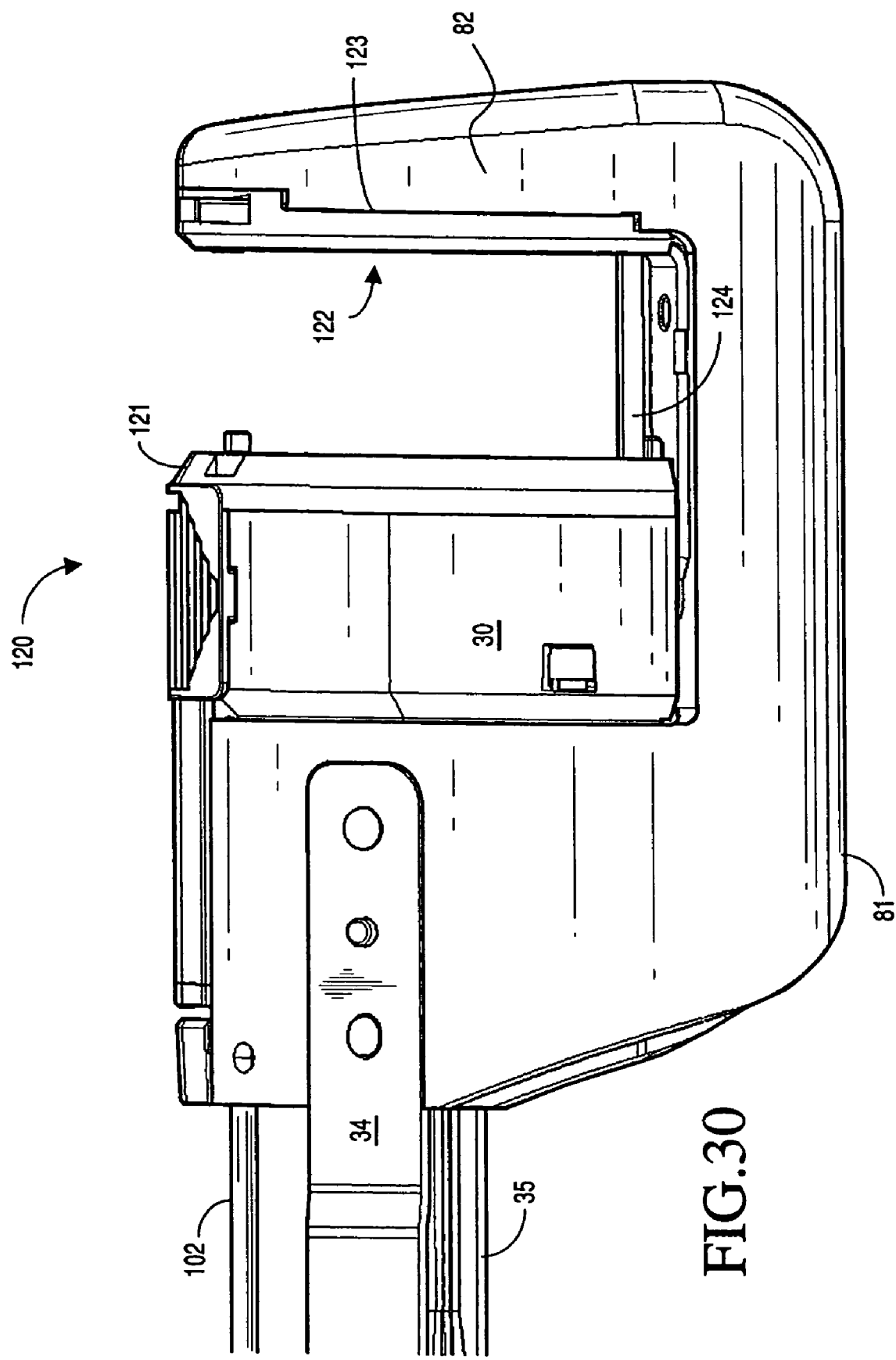
FIGS. 30–38 show the various steps involved in the actuation of the present linear surgical stapler.

The retainer 160 can now be removed from the end effector 80. Specifically, completion of loading the cartridge module 120 causes the disengagement tab 165 to contact the supporting structure 81 (See FIG. 23), resulting in an upward movement of the spring arm 162 when the cartridge module 120 is fully loaded as in FIG. 24. This upward movement displaces containment slots 164 upward such that the guide pin 124 is no longer contained (see FIGS. 25 and 26). Referring now to FIGS. 27 to 29, a removal force applied to the thumb pad 166 results in the retainer 160 pivoting outward about protrusion 159 until the groove 161 is able to slip off protrusion 159. Removal of the retainer 160 allows for the loaded linear surgical stapler 20 to be utilized.

Figure 15:
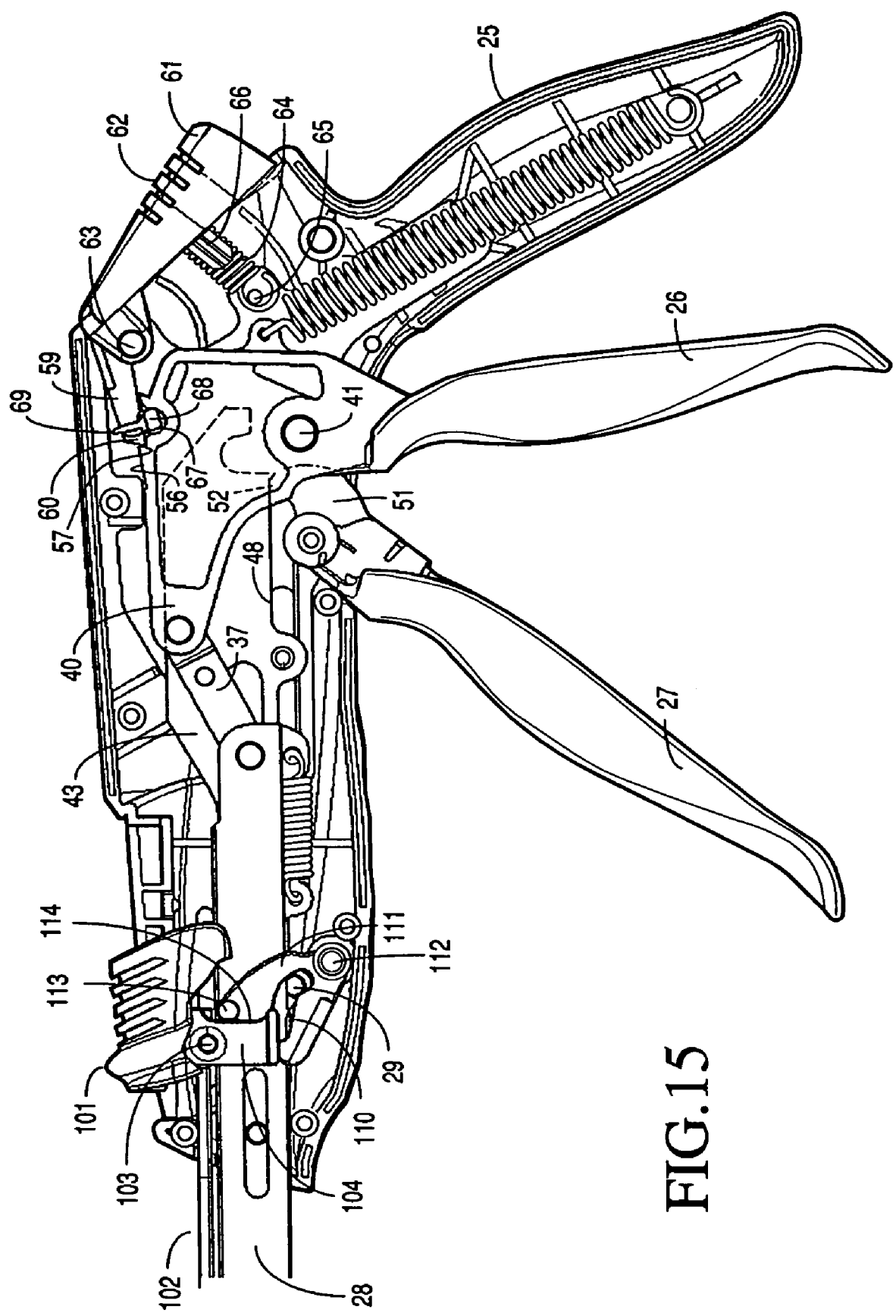
FIG. 15 is a partial cross sectional view of the linear surgical stapler with the closure trigger slightly retracted.

In FIG. 15, the closure trigger 26 has been partially squeezed from its open, unactuated position illustrated in FIGS. 1 and 13. When the closure trigger 26 is partially squeezed, it pivots about the closure trigger pivot pin 41 in a counterclockwise direction toward the handgrip 24. As it pivots, the slotted closure arm link 40 and closure plate closure links 36, 37 move forwardly, consequently moving the closure member 28 and firing bar 43 distally. As the slotted closure arm link 40 moves forwardly, the pall lug 60 of the release pall 59 slides on the clamp sliding surface 56. The pall lug 60 engages the distal ends of the toggle arms 69 of the toggles 68, and consequently pivots the toggles 68 in a clockwise direction. As the slotted arm closure link 40 continues to move forwardly in response to the pivotal movement of the closure trigger 26 toward the handgrip 24, the pall lug 60 of the release pall 59 will eventually lodge into the intermediate detent 57. Once positioned in the intermediate detent 57, the closure spring 42 is incapable of returning the closure trigger 26 to its original, unactuated position. The closure trigger 26 is now in its intermediate, partially closed position, to properly position and retain tissue between the cartridge housing 121 and anvil 122, as shown in FIG. 15. In addition, as the closure member 28 and firing bar 43 move distally, the apex 52 of the arcuate firing trigger link 51 slides on the sliding surface 48 of the proximal end section 47 of the firing bar 43.

During the closing stroke from the open to the intermediate position the retaining pin mechanism 100 is activated. Forward movement of the closure member 28 moves the integral posts 29 distally. The posts 29 contact the L-shaped slot 110 of the yoke 111. Hence, distal movement of the posts 29 cam the L-shaped slot 110 causing the yoke to pivot around pins 112. The rotation brings bearing posts 113 on the yoke 111 into contact with camming surfaces 114 on the push rod driver 104. Further rotational movement of the yoke 111 causes bearing posts 113 to move the push rod driver 104 distally through camming contact on surfaces 114. The push rod driver 104 contacts the push rod 102, moving the push rod 102 distally. The push rod 102, in turn, moves the coupler 133 and retaining pin 125 distally. Completion of the closing stroke to the intermediate detent 57 position results in the retaining pin 125 moving distally through the hole 144 of the cartridge housing 121, through hole 159 running through the washer 123 and anvil 122 and into the hole (not shown) in the supporting structure 81. Tissue, which was disposed between the contact surface 127 of the cartridge housing 121 and the anvil 122, is now trapped between retaining pin 125 and the guide pin 124.

This same result can be obtained prior to closing by manual distal movement of saddle slide 101. Slide movement will result in forward movement of the push rod 102, coupler 133 and retaining pin 125 until the retaining pin 125 is fully disposed through the anvil 122, washer 123 and hole 89 in the supporting structure 81. Activation of the closing stroke after the retaining pin 125 has been manually moved forward would still result in the rotation of the yoke 111 as described above but without any additional movement of the retaining pin actuation mechanism 100.

Figure 32:
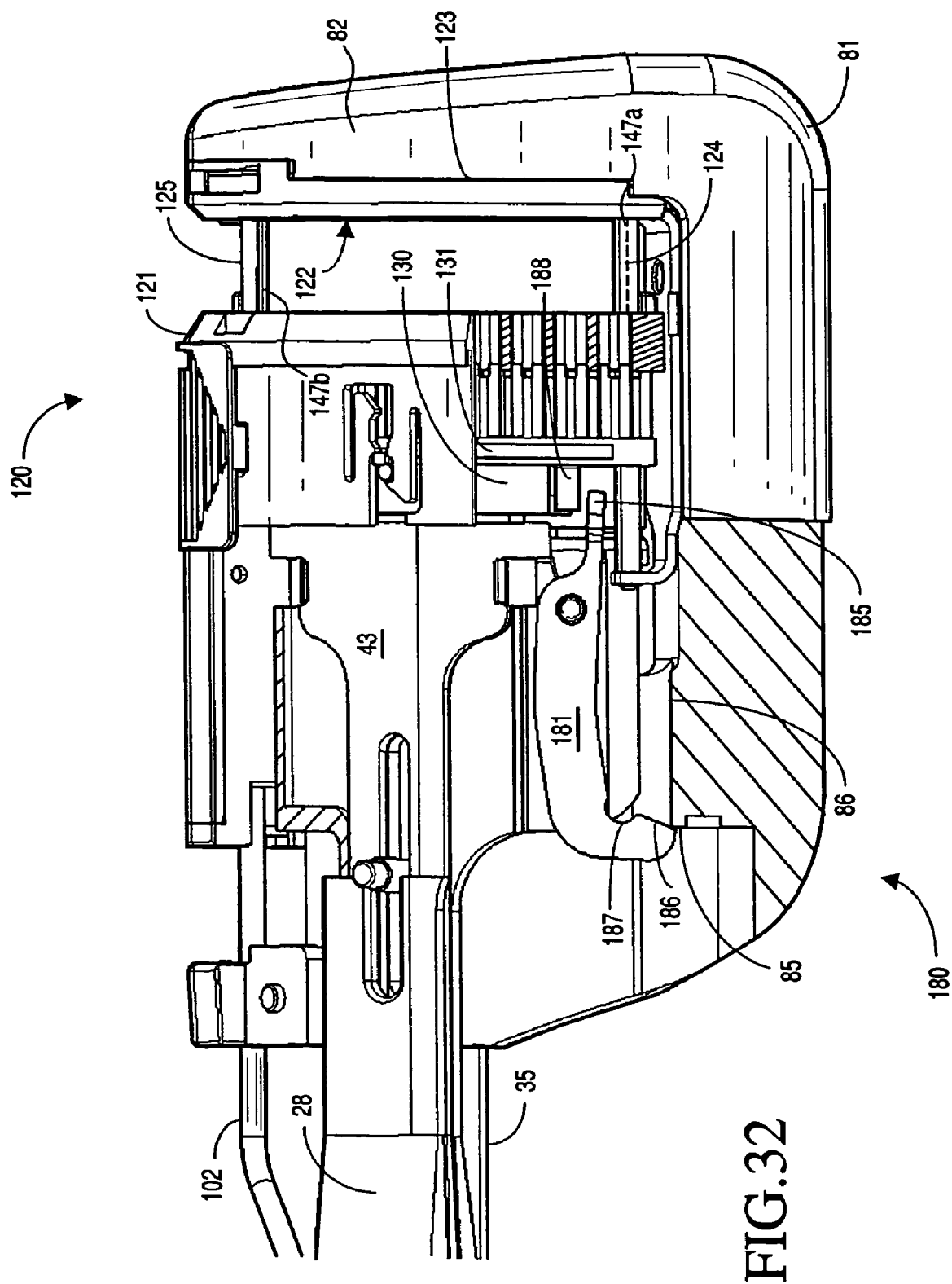

The closing stroke from the open to the intermediate detent 57 position moves the lockout lever 181 distally as it is attached to closure member 28 by the pin 182 as shown in FIG. 31 (open) and FIG. 32 (intermediate position). Distal movement of the lockout lever 181 causes the camming surface 186 to contact the lockout ledge 85 of the support 81, resulting in the lockout lever 181 rotating clockwise and coming to slidable contact with base surface 86 of supporting structure 81. In this position, the distal end 185 of the lockout lever 181 has rotated away from post 188 on driver 131.

Figure 16:
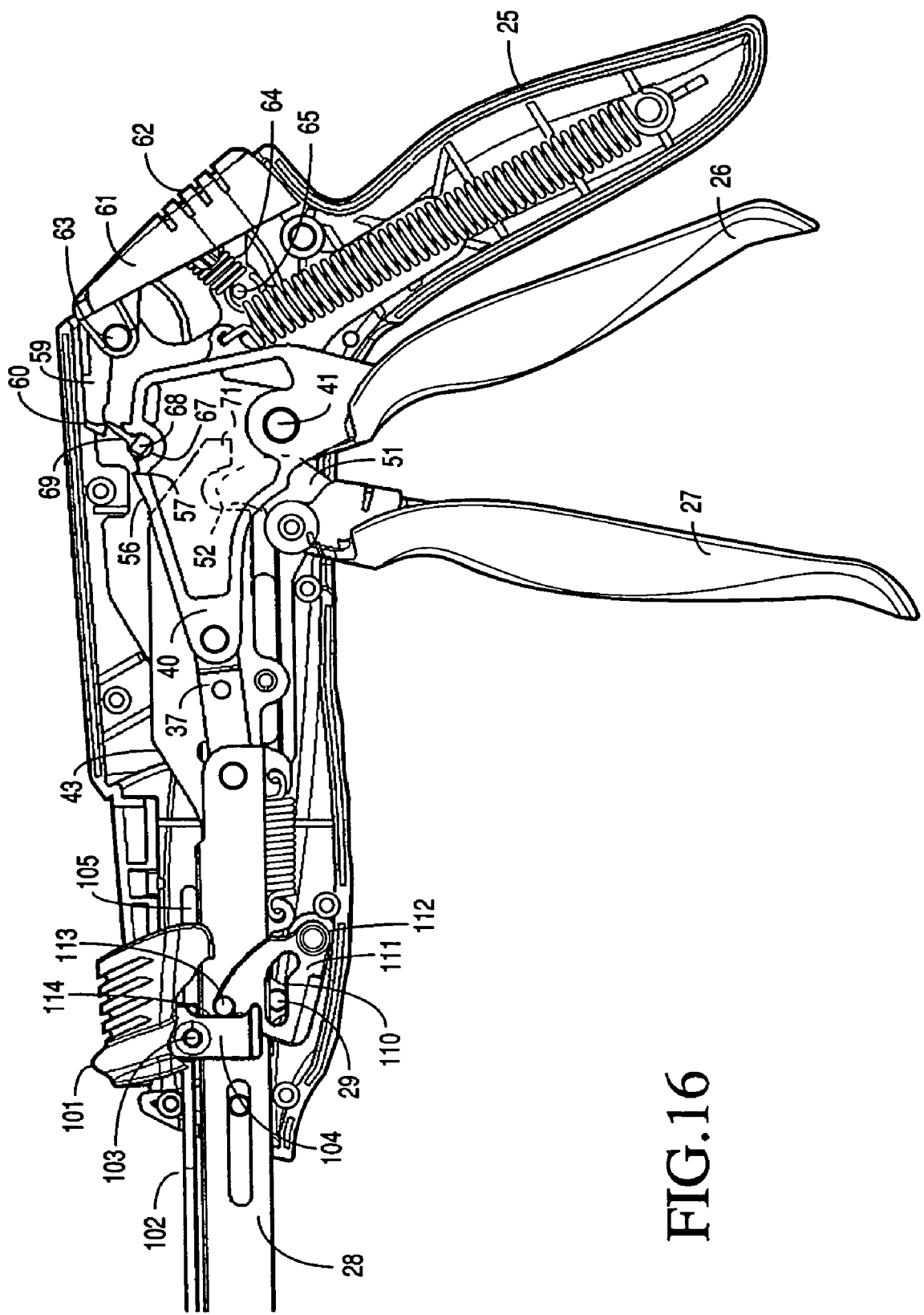
FIG. 16 is a partial cross sectional view of the linear surgical stapler with the closure trigger nearly fully retracted.

Referring now specifically to FIG. 16, when the closure trigger 26 is squeezed toward the handgrip 24 from the intermediate detent 57 position, the toggle arms 69 of the toggle 68 disengage from the pall lug 60. Consequently, as the toggle 68 continues to rotate in a clockwise direction, the release pall lug 60 rides up the toggle arms 69 and with continued motion of the closure trigger 26 falls into the closure detent 58. As the release pall 59 rides up the toggle arm 69 it rotates the release button 61 clockwise around pivot 63. As the release pall 60 falls into closure detent 58, it makes an audible clicking sound alerting the surgeon that closure position has been reached.

In addition, as the firing bar 43 continues to move forwardly, the apex 52 of the arcuate firing trigger link 51 comes into contact with the side engagement surface 49 of the proximal end section 47 of the firing bar 43. Consequently, the firing trigger 27 is moving into a position where it can continue to move the firing bar 43 distally to fire staples after the tissue has been fully clamped. When the apex 52 of the arcuate firing trigger link 51 moves into engagement with the engagement surface 49 of the proximal end section 47, the firing trigger 27 begins to pivotally rotate in a counterclockwise direction toward the hand grip 24 in response to the action of a torsion spring on the right hand side of the firing trigger 27 (torsion spring not shown). The firing trigger 27 pivots independently of the pivotal movement of the closure trigger 26, but its pivotal rotation is blocked until the firing bar 43 has moved distally to enable engagement of the firing trigger link 51 with the terminal engagement surface of the firing bar 43.

Figure 17:
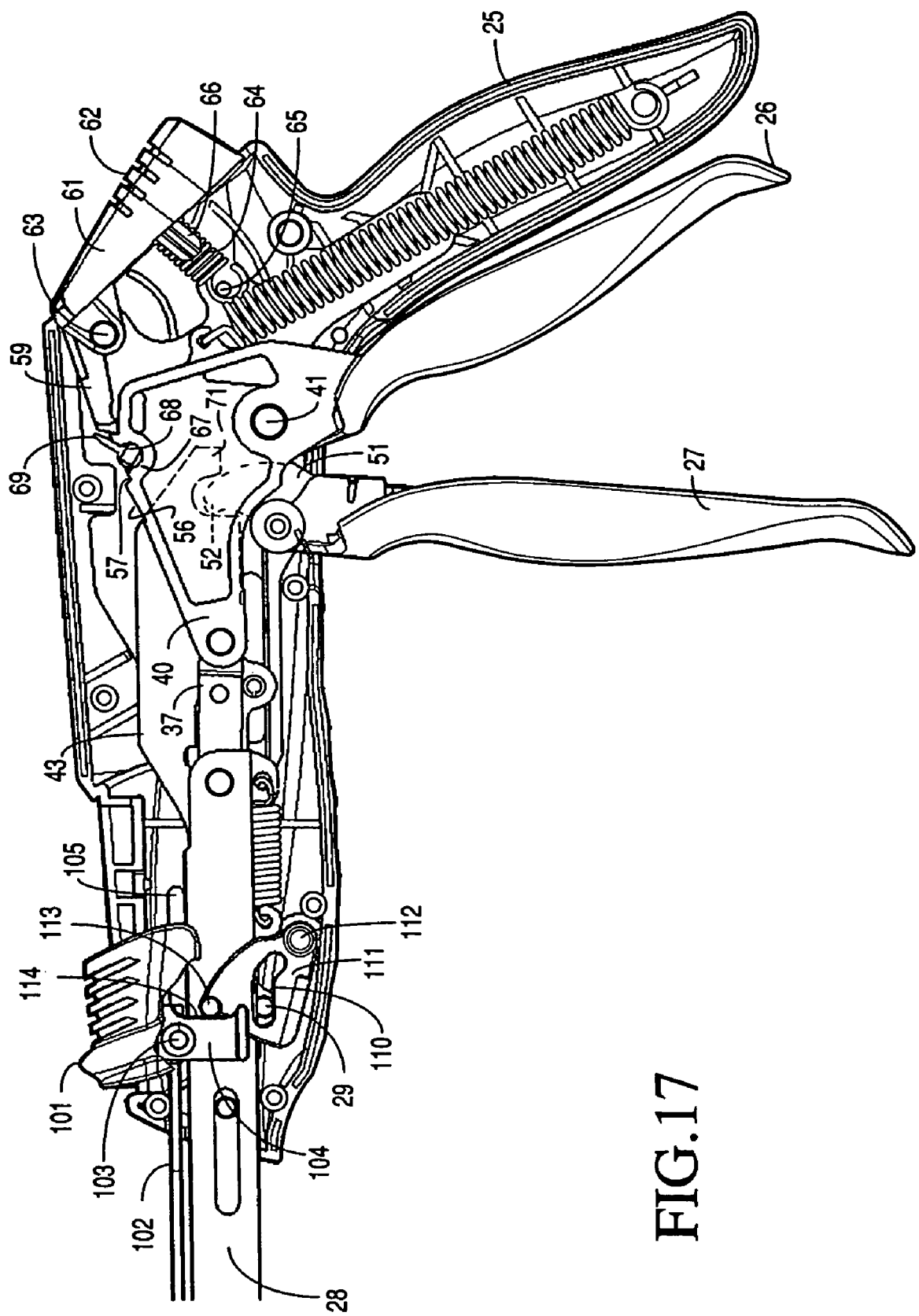
FIG. 17 is a partial cross sectional view of the linear surgical stapler with the closure trigger fully retracted.

Turning specifically to FIG. 17, when the closure trigger 47 has been fully squeezed and it is adjacent the handgrip 24, the pall lug 60 at the distal end of the release pall lodge 59 into the closure detent 58. In the closure detent 58 position, the tissue has been fully clamped between the cartridge housing 121 and anvil 122, and the closure spring 42 is incapable of returning the closure trigger 26 to its original position. Therefore, the closure trigger 26 is retained in the position shown in FIG. 4.

Concurrently with the counterclockwise motion of the closure trigger 26, the firing trigger 27 continues to rotate counterclockwise by the action of the torsion firing bar return spring 55 until the firing trigger 27 is in a relatively vertical orientation with respect to the handle 21 of the linear surgical stapler 20. In the fully clamped position, the apex 52 of the arcuate firing trigger link 51 has fully engaged the engagement surface of the proximal end section 47 of the firing bar 43 and, therefore, the firing trigger 27 is in a position to further move the firing bar 43 distally to fire staples into the tissue.

Figure 33:
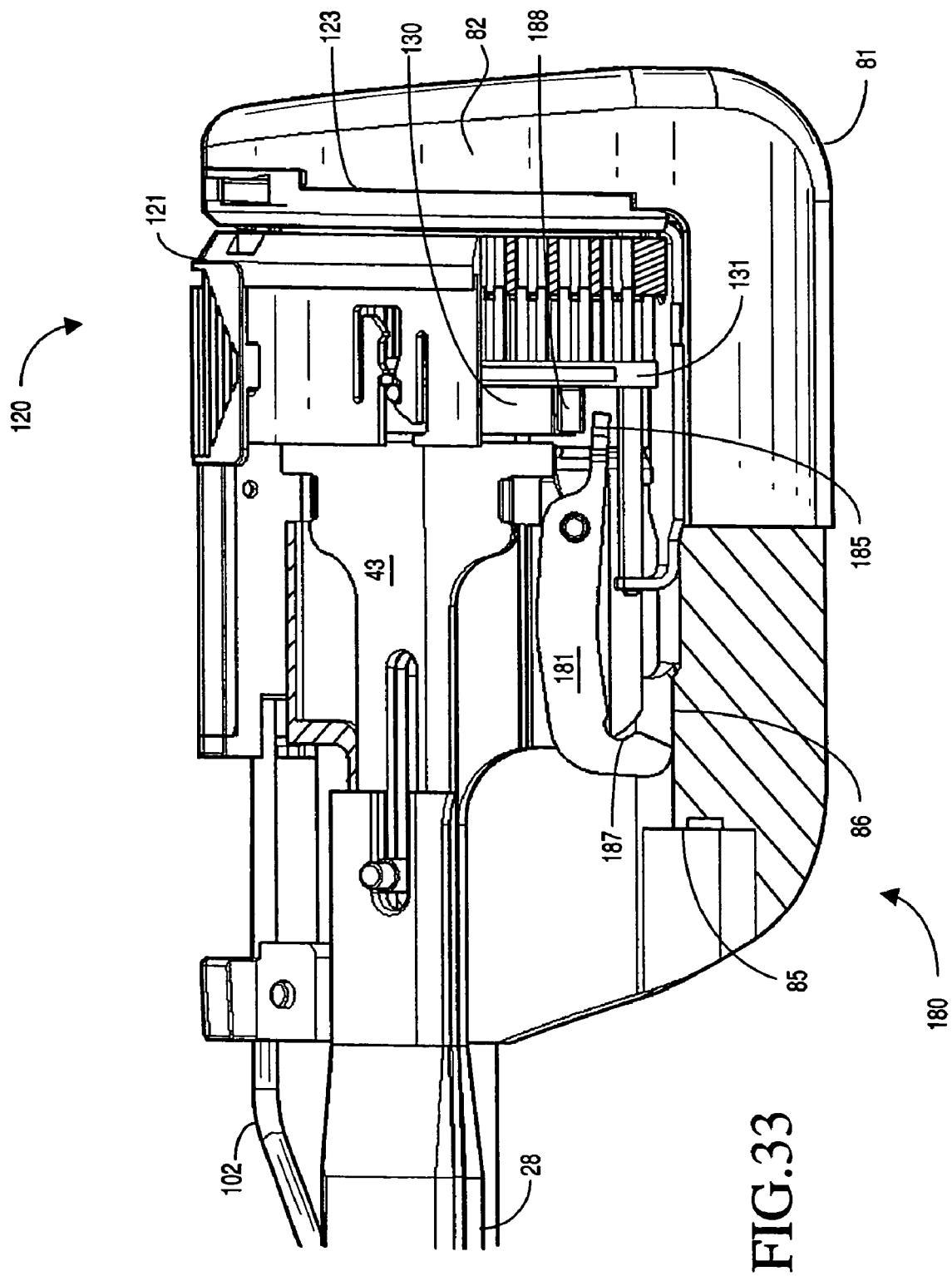

In the fully closed position the staple pockets 128 of the cartridge housing 121 are aligned with the staple-forming surface 129 of the anvil 122 as shown in FIG. 33. The retaining pin 125 has aligned the top of the anvil 122 and the cartridge housing 121 and the guide pin 124 has aligned the bottom of the cartridge housing 121 with the bottom of the anvil 122.

Figure 18:
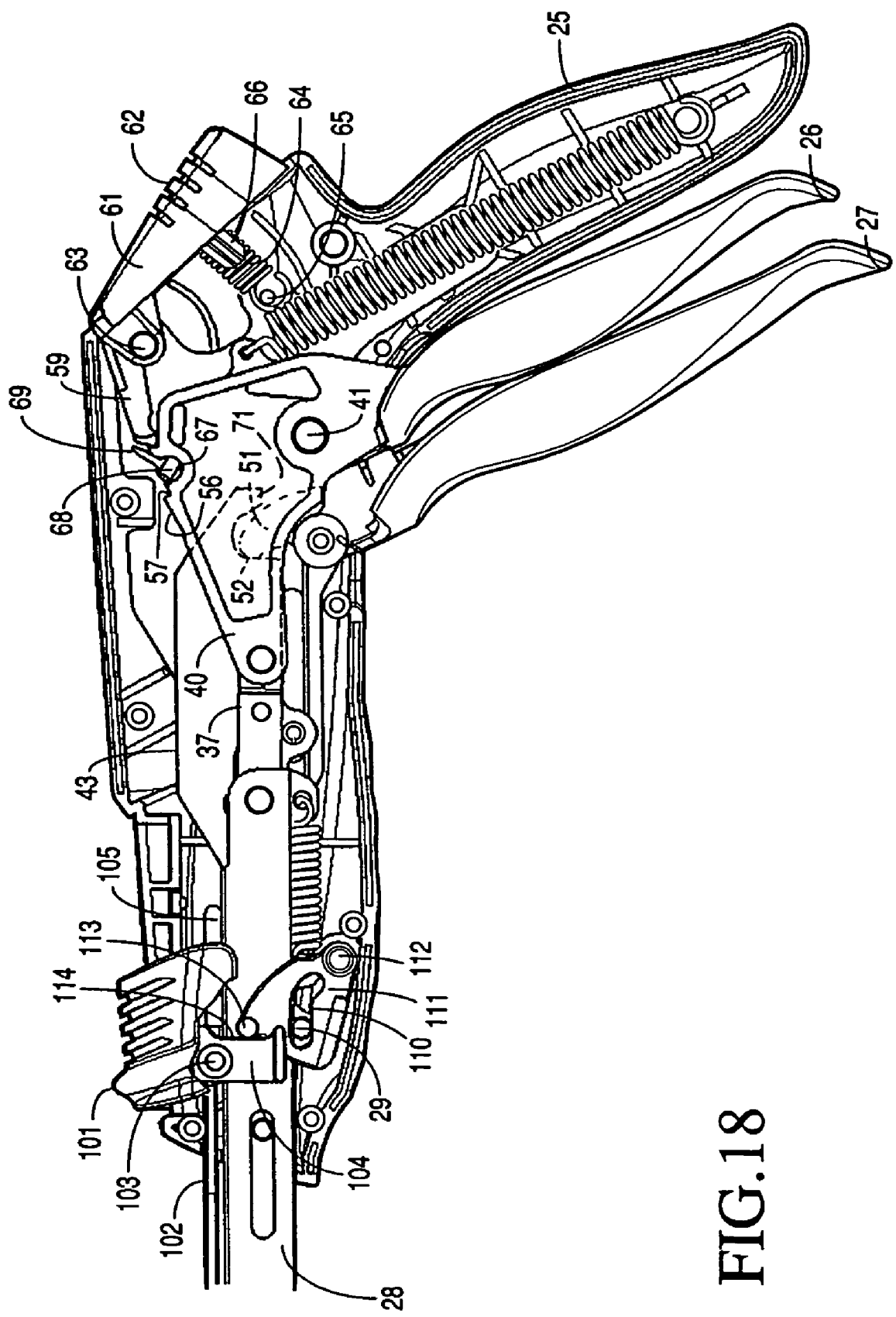
FIG. 18 is a partial cross sectional view of the linear surgical stapler with the firing trigger and closure trigger fully retracted.
Figure 34:
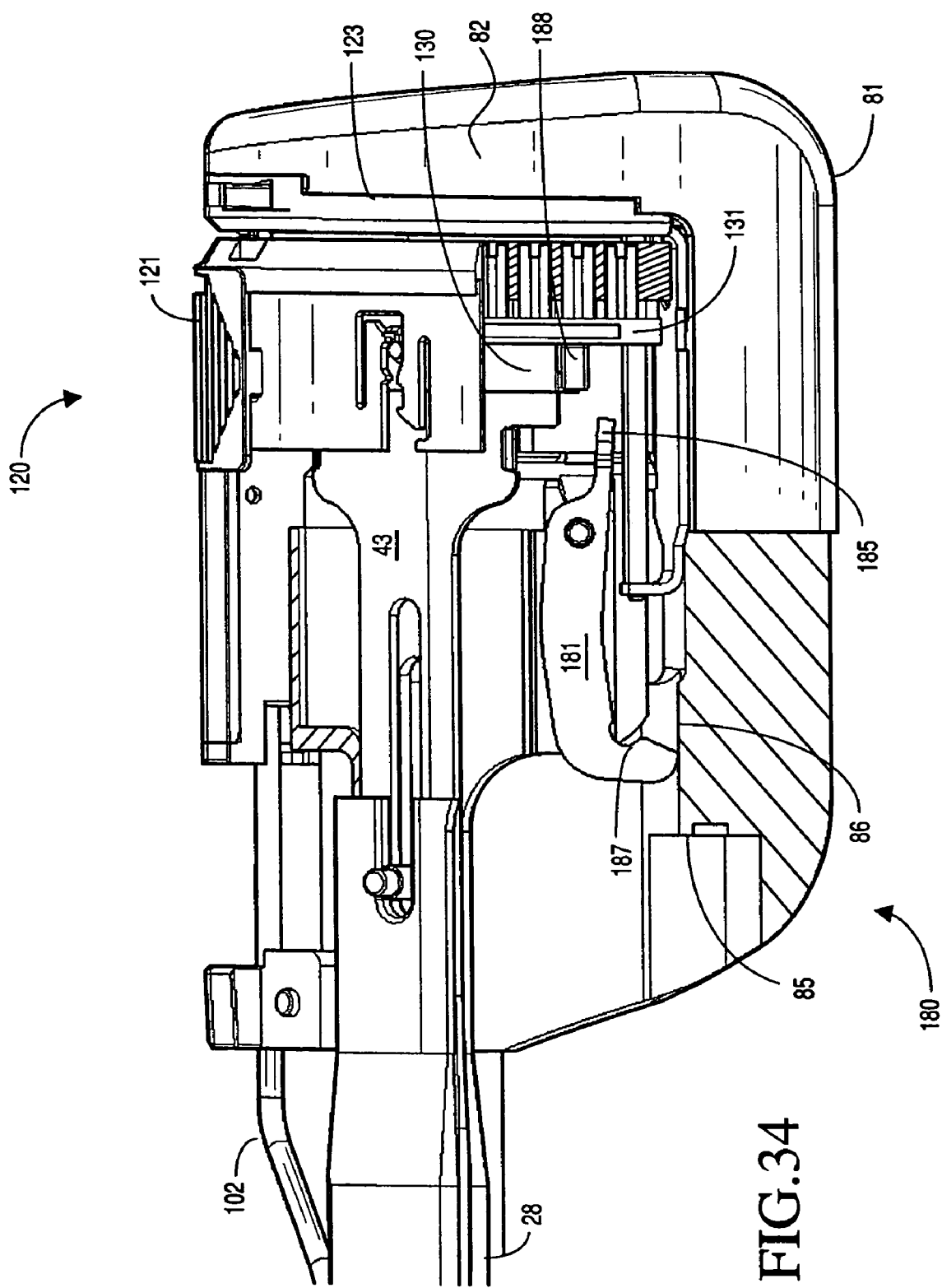

As illustrated in FIG. 18 and FIG. 34, the firing trigger 27 can be squeezed to pivotally rotate it toward the hand grip 24 until it is positioned adjacent the closure trigger 26. During the pivotal rotation of the firing trigger 27, the firing bar 43 moves distally, contacts the knife holder 130. The resulting distal movement of the knife holder 130 results in contact with the knife 126 and driver 131. Distal movement of the driver 131 results in the staples (not shown) to be distally advanced into the staple forming surfaces 129 of the anvil 122 resulting in staple formation of a generally B shape. The knife 126 distally advances in slots 147 of the guide pin 124 and the retaining pin 125 in conjunction with staple formation. These slots 147 guide the knife 126 onto the cutting surface 157 of cutting washer 123 resulting in the transection of any tissue caught between.

Figure 35:
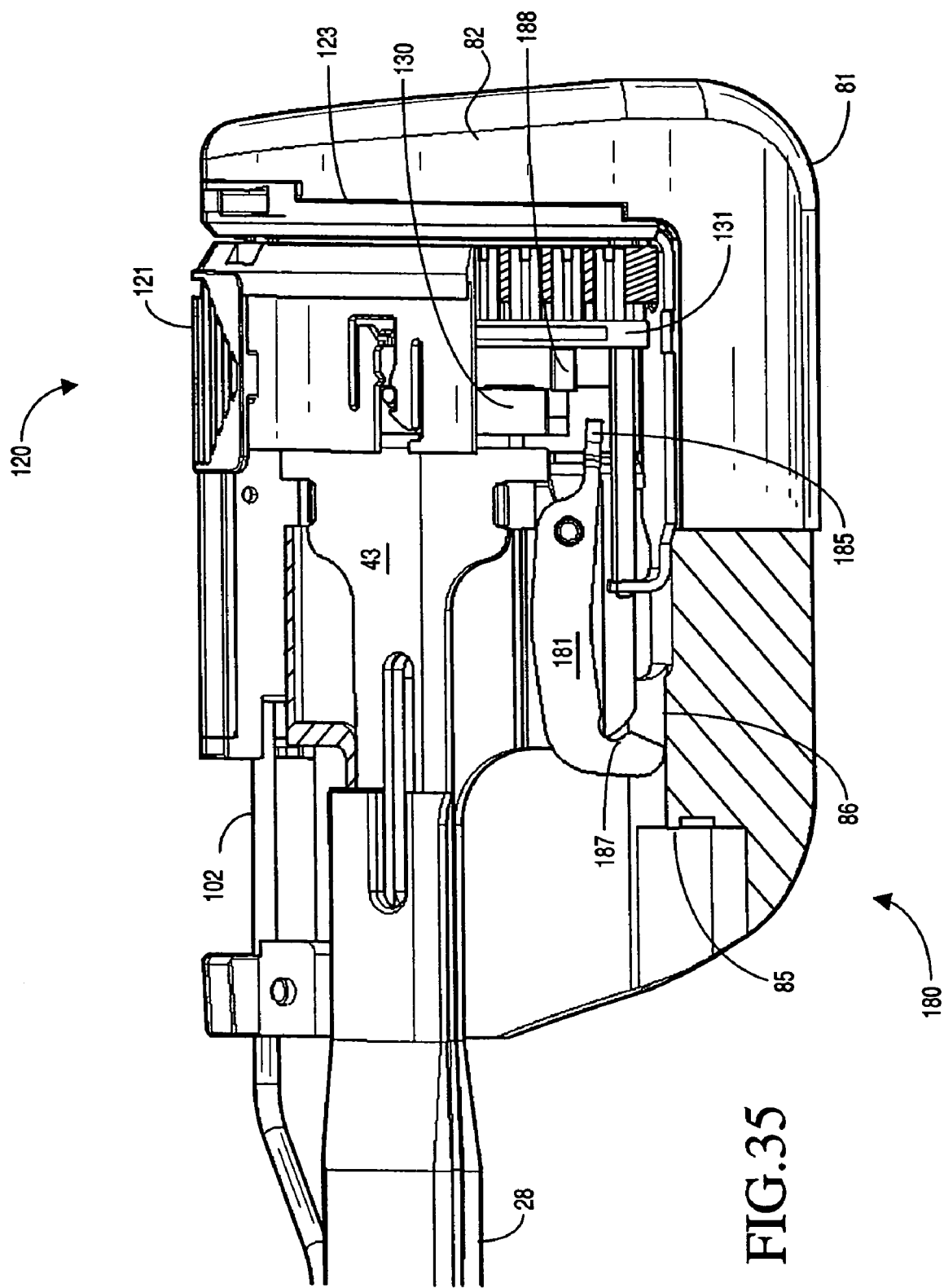

Release of manual pressure to the firing trigger 27 results in the firing bar return spring 55 to retract the firing bar 43 and returns the firing trigger 27 to the position shown in FIG. 17. This movement results in the retraction hook 45 retracting the retraction ledge 173 on the knife holder 130 and knife 126. The resulting proximal movement retracts the knife 126 into the cartridge housing 121 as shown in FIG. 35. Detent post 138 on the knife holder 130 retracts into engagement with the detent 139 on the cartridge housing 121 to hold the knife holder 130 and knife 126 in this retracted position. The driver 131 is retained in its distal most (fired) position by engagement of the detent post 140 on the driver 131 engaging detent 142 of the cartridge slot 137.

Should there be an interference on the knife 126, as from the user cutting into another surgical instrument by mistake, such that the force from the firing bar return spring 55 is insufficient to retract the firing bar 43 and thus retract the knife 126 into the cartridge housing 121, the user can manually retract the cutting system by pulling clockwise on the firing trigger 27. The manual clockwise movement causes the arcuate firing trigger link 51 to rotate clockwise until it strikes a firing bar retraction tab 71 on the proximal end 47 of the firing bar 43. The contact between the clockwise moving arcuate firing trigger link 51 and the firing bar retraction tab 71 causes the firing bar 43 to retract proximally and return to the position shown in FIG. 17. This in turn causes the retraction hook 45 retract the retraction ledge 173 on the knife holder 130 and knife 126. Thus, this safety feature allows for the user to retract the cutting mechanism to a safe position and return the firing system to a position that would allow the linear surgical stapler 20 to be opened, as will now be described.

Figure 19:
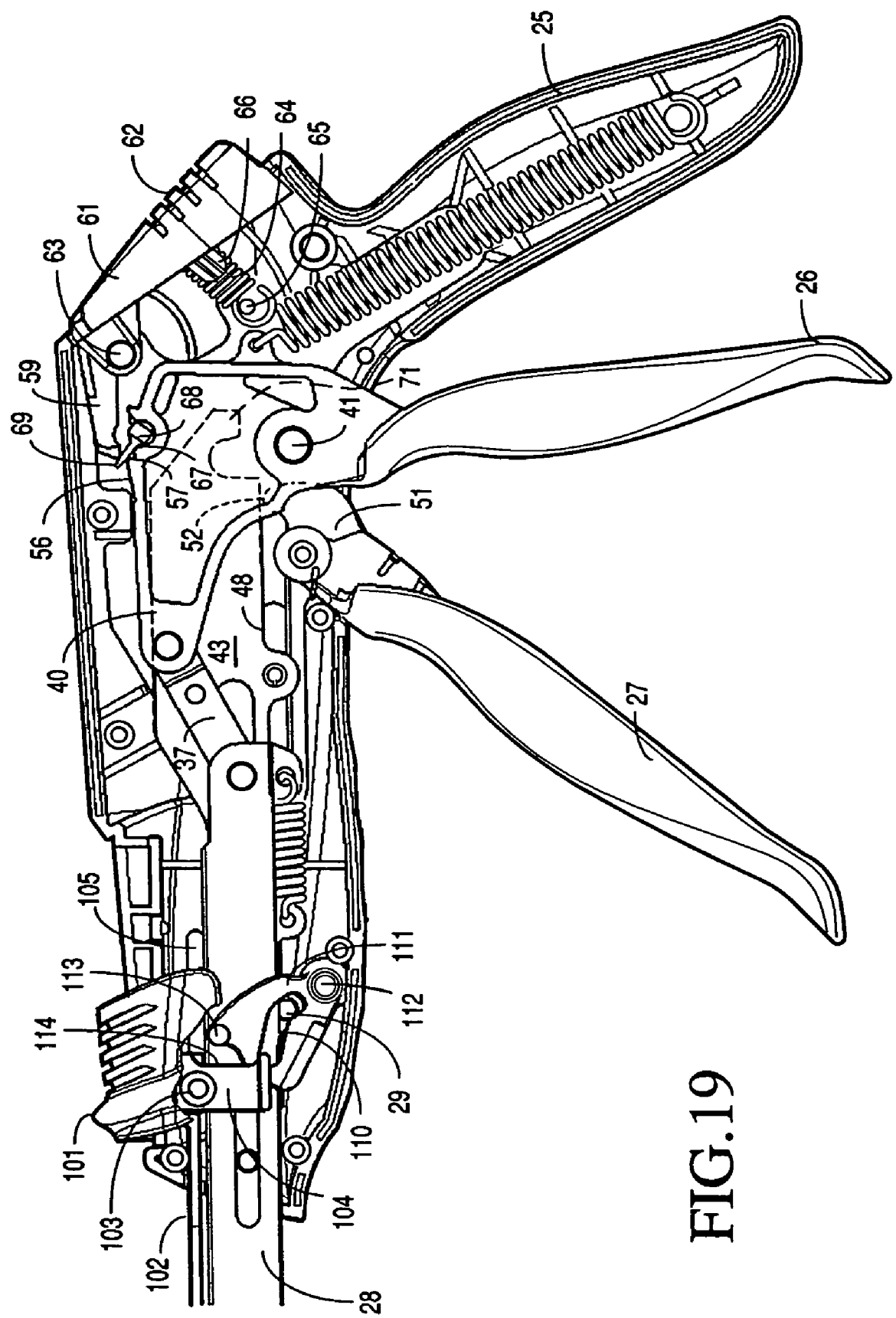
FIG. 19 is partial cross sectional view of the linear surgical stapler after the surgeon depresses the release button.

Referring to FIG. 19, when the surgeon depresses the release button 61, the release pall 59 pivots about a release trunnion 63 in a clockwise direction to dislodge the pall lug 60 from the closure detent 58 position. As it is dislodged, the pall lug 60 rides on the toggle arms 69 to bypass the intermediate detent position 57 on clamp link 40. In this manner, the closure and firing triggers 26, 27 can return to their original, unactuated positions in response to the bias created from the closure spring 42 and firing bar return spring 55. When the pall lug 60 rides on the toggle arms of the toggles 68, the toggle arms 69 rotate counterclockwise as the closure and firing triggers 26, 27 rotate in a clockwise direction to return to their original unactuated positions. Therefore, the surgeon can release the closure and firing triggers 26, 27 so that they can return to the positions illustrated in FIG. 20 without unnecessarily returning to the intermediate detent 57 position.

Figure 20:
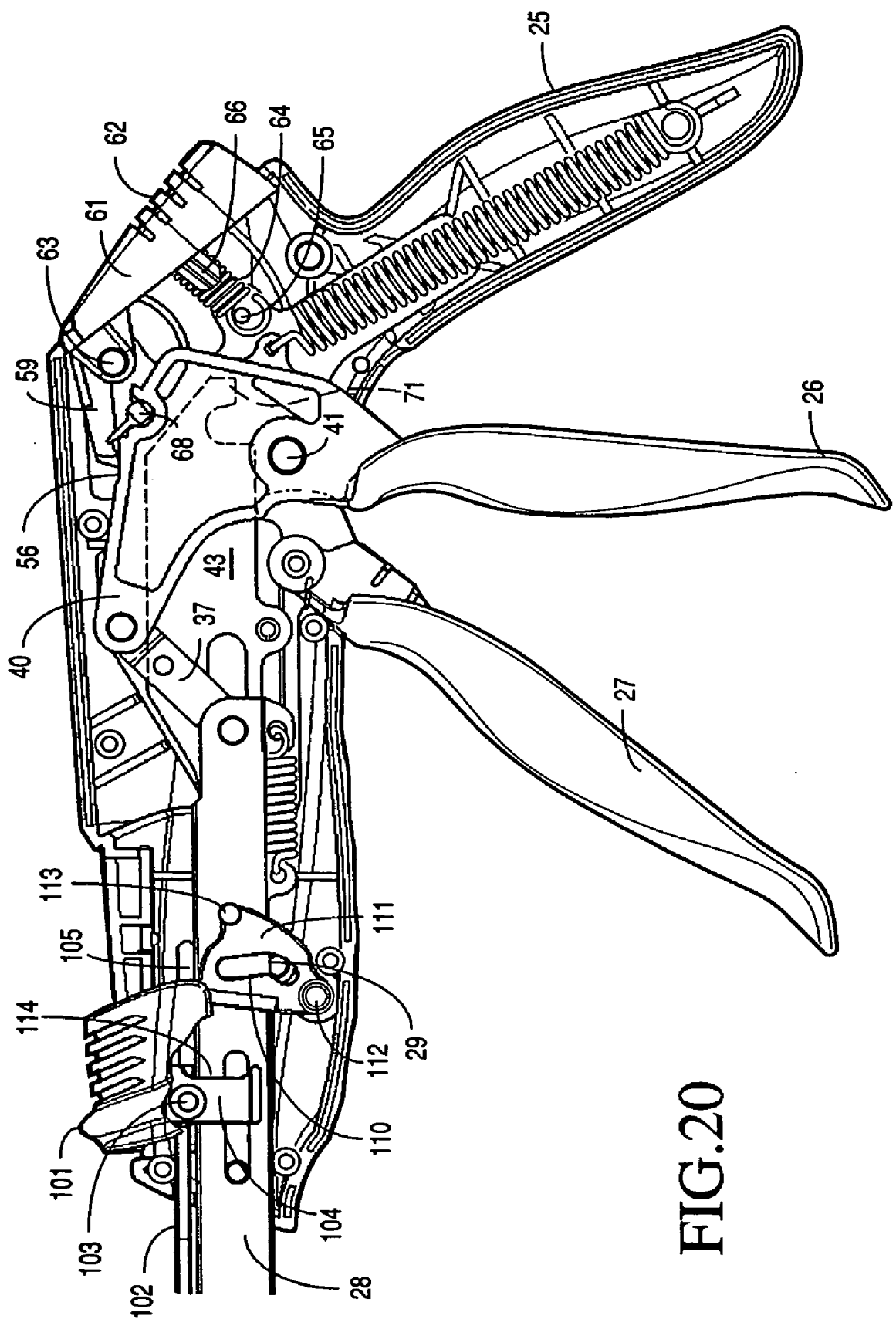
FIG. 20 is a partial cross sectional view of the linear surgical stapler upon release of the closure and firing triggers without returning to an intermediate detent position.
Figure 21:
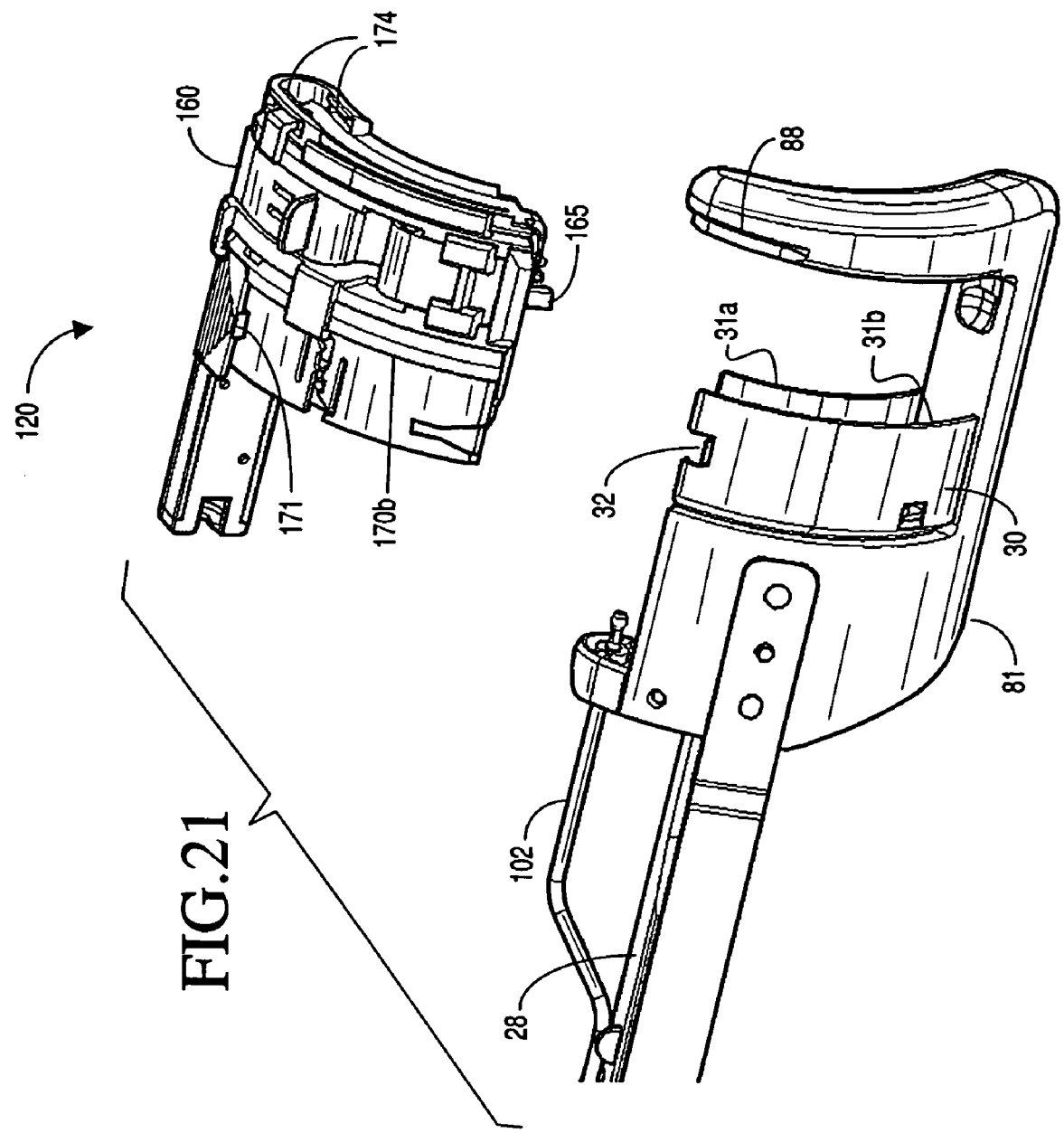
FIG. 21–29 show the insertion of a cartridge module and the removal of the retainer.
Figure 36:
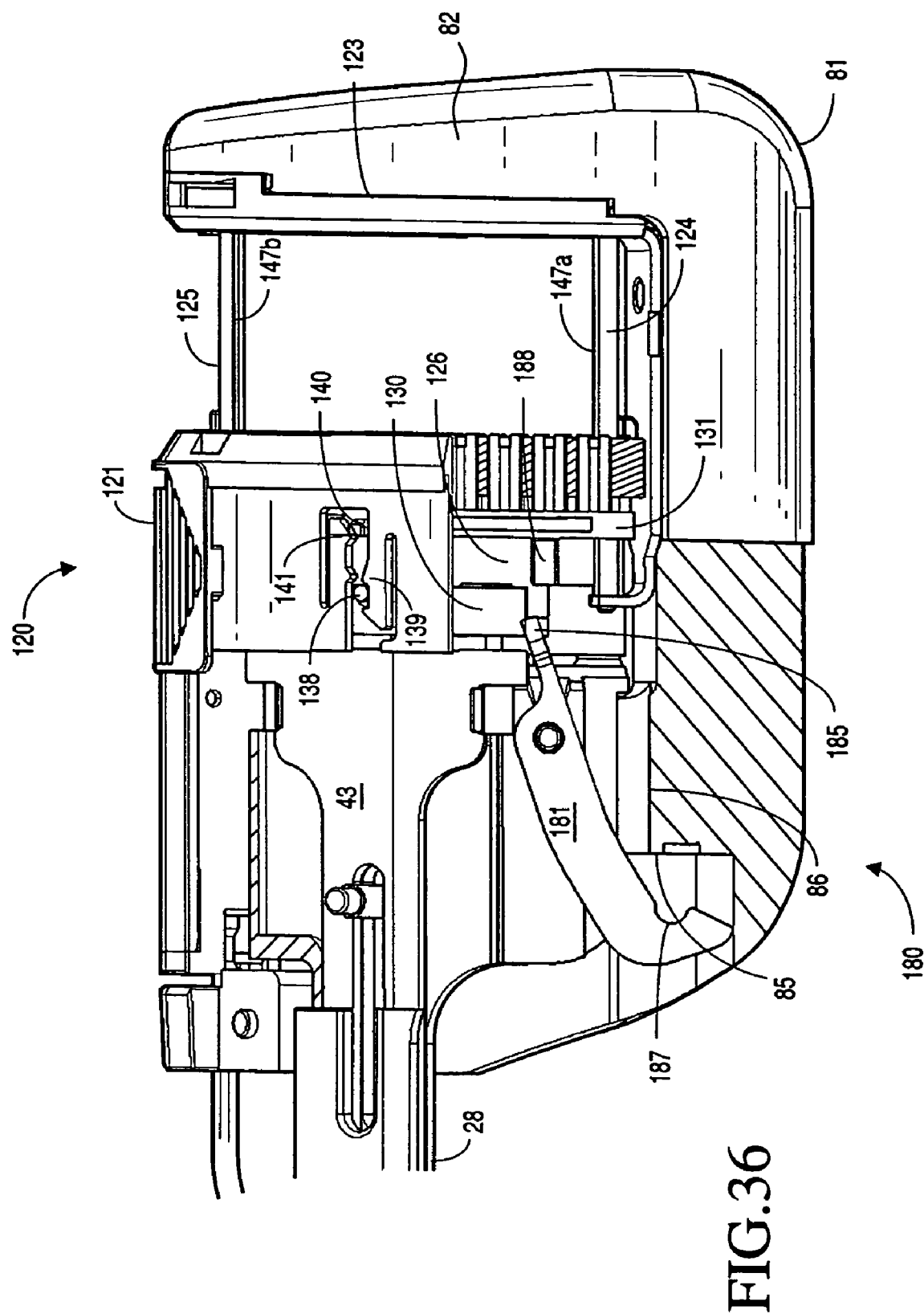

The release of the linear surgical stapler 20 to the open position shown in FIG. 20 causes the closure member 28 and the attached lockout lever 181 to retract to the full open position as shown in FIG. 36. In this position the post 188 on the driver 131 is no longer disposed to hold down the lockout lever distal end 185. The driver 131, as described above, has been detented into place in the forward position by post 140 and the cartridge detent 142. Hence, when the lockout lever 181, whose proximal end 184 slides along support arm surface 86, is fully retracted it is now free to rotate counter-clockwise and drop lockout groove 187 below ledge 85 on the C-shaped supporting structure 81. The lockout lever 181 will remain in this position when the cartridge module 120 is removed as shown in FIG. 37.

Figure 38:
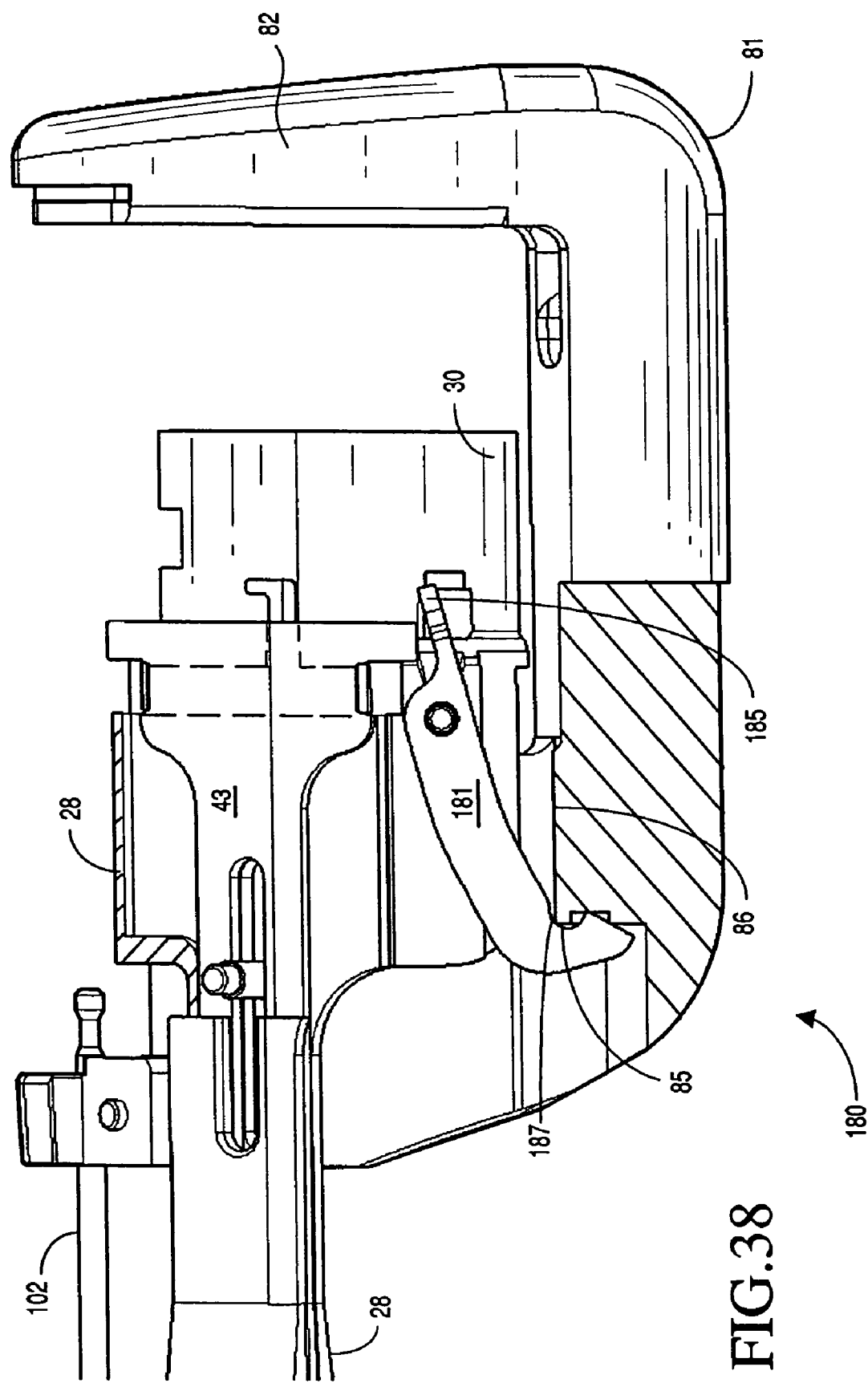
Figure 39:
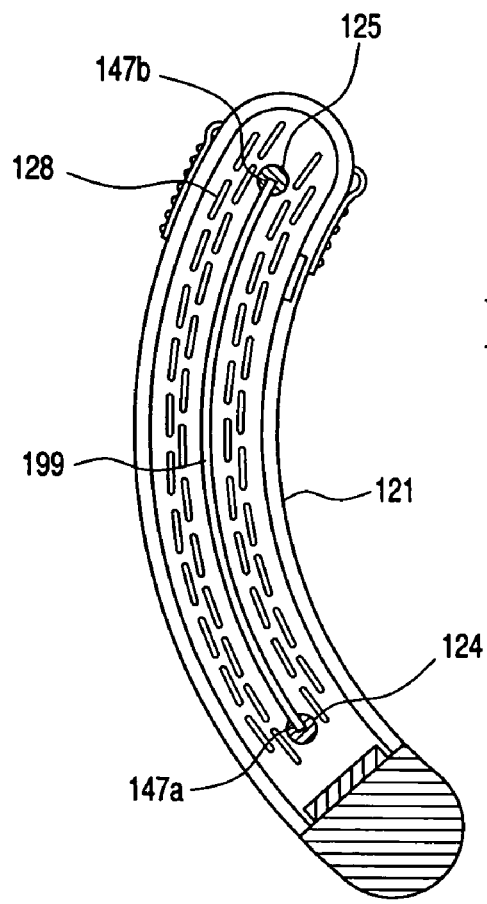
FIGS. 39 and 40 are detailed front views of the cartridge housing.
Figure 40:
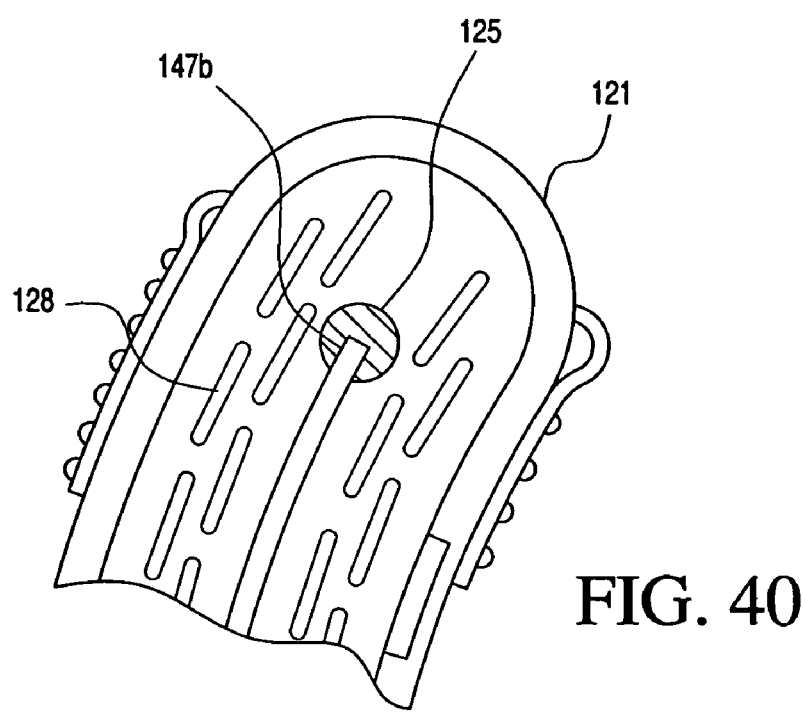

Any future attempt to close the linear surgical stapler 20 which has been fired will result in the lockout groove 187 hooking into the ledge 85 as shown in FIG. 38, supplying feedback to the user of a previously fired device. This same feature will engage if the retainer 160 has been removed prior to loading and the cartridge module 120 has been misloaded without the cartridge module 120 being in the right position. In this case the driver post 188 would not be in the right position to move lockout lever 181 into the position to be cammed up onto surface 86 as described above. Similarly, a cartridge module 120 which has already been fired would also not release the lockout mechanism 180. It is important to note that there is closure stroke travel allowed in the lockout mechanism 180 prior to engagement of the lockout groove 187 hooking into the ledge 85. This travel indicates to the user that the device is not jammed due to some malfunction as might be the reaction if the lockout mechanism 180 had no travel. Hence, the user knows that the device is not jammed but incorrectly loaded when the lockout mechanism engages.

After release of the device back to the open position shown in FIGS. 1 and 2, the retaining pin mechanism 100 must be manually retracted by pulling proximally on saddle 101. The retraction causes the retaining pin 125 to retract back into the cartridge housing 121. At the completion of the manual retraction the fired cartridge module 120 can be unloaded and replaced with a new cartridge module 120.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A surgical instrument adapted for applying a plurality of surgical fasteners to body tissue, the surgical instrument comprising:
    a cartridge module including a cartridge housing containing a plurality of surgical fasteners and a knife, the cartridge module includes a driver disposed to push surgical fasteners out of the cartridge housing;
    a firing mechanism associated with the cartridge housing for ejecting the surgical fasteners and the knife from the cartridge housing; and
    the knife includes a detent disposed to contact a mating detent of the cartridge module during longitudinal travel of the knife thereby preventing undesired forward and rearward motion of the knife;
    the driver includes a detent disposed to contact at least one mating detent formed on the cartridge module for preventing undesired movement of the driver; and
    wherein the cartridge housing includes a cartridge slot through which the detent of the knife extends, the cartridge slot includes first and second flexible fingers molded into the side of the cartridge housing.

2. The surgical instrument according to claim 1, wherein the first and second fingers are oriented parallel to the longitudinal axis of the cartridge module.

3. The surgical instrument according to claim 1, wherein the first finger is shaped and dimensioned to contact the detent of the knife.

4. The surgical instrument according to claim 1, wherein the second finger is shaped and dimensioned to contact the detent of the driver.

5. The surgical instrument according to claim 1, wherein cam surfaces are positioned along the edge of each of the first and second fingers.

6. The surgical instrument according to claim 5, wherein the location of the respective cam surfaces is determined by the desired position of the driver or knife during operation.

7. A surgical instrument adapted for applying a plurality of surgical fasteners to body tissue, the surgical instrument comprising:
    a cartridge module including a cartridge housing containing a plurality of surgical fasteners and a knife, the cartridge module includes a driver disposed to push surgical fasteners out of the cartridge housing;

a firing mechanism associated with the cartridge housing for ejecting the surgical fasteners and the knife from the cartridge housing;

means for preventing undesired forward and rearward motion of the knife to prevent the knife from inadvertently moving; and means for preventing undesired movement of the driver.

8. The surgical instrument according to claim 7, wherein the means for preventing undesired movement of the driver prevents the driver from moving prior to use so that surgical fasteners are not inadvertently fired.

9. The surgical instrument according to claim 7, wherein the means for preventing undesired forward and rearward motion of the knife includes a detent disposed to contact a mating detent of the cartridge module during the longitudinal travel of the knife and the means for preventing undesired movement of the driver includes a detent disposed to contact at least one mating detent formed on the cartridge module.

10. The surgical instrument according to claim 9, wherein the cartridge housing includes a cartridge slot through which the detent of the knife extends, the cartridge slot includes first and second flexible fingers molded into the side of the cartridge housing.

11. The surgical instrument according to claim 10, wherein the first and second fingers are oriented parallel to the longitudinal axis of the cartridge module.

12. The surgical instrument according to claim 10, wherein the first finger is shaped and dimensioned to contact the detent of the knife.

13. The surgical instrument according to claim 10, wherein the second finger is shaped and dimensioned to contact the detent of the driver.

14. The surgical instrument according to claim 10, wherein cam surfaces are positioned along the edge of each of the first and second fingers.

15. The surgical instrument according to claim 14, wherein the location of the respective cam surfaces is determined by the desired position of the driver or knife during operation.

16. A surgical instrument adapted for applying a plurality of surgical fasteners to body tissue, the surgical instrument comprising:

a cartridge module including a cartridge housing containing a plurality of surgical fasteners and a knife, the cartridge module includes a driver disposed to push surgical fasteners out of the cartridge housing;

a firing mechanism associated with the cartridge housing for ejecting the surgical fasteners and the knife from the cartridge housing;

means for preventing undesired forward and rearward motion of the knife to prevent the knife from inadvertently moving; and wherein the driver includes a prefired position and a retracted position and means are operatively associated with the driver for securing the driver in the prefired position and means are operatively associated with the driver for securing the driver in the retracted position.

17. The surgical instrument according to claim 16, wherein the means for preventing undesired forward and rearward motion of the knife includes a detent disposed to contact a mating detent of the cartridge module during the longitudinal travel of the knife and the means for securing the driver in the prefired position and the means for securing the driver in the retracted position includes a detent disposed to contact at least one mating detent formed on the cartridge module.

18. The surgical instrument according to claim 17, wherein the cartridge housing includes a cartridge slot through which the detent of the knife extends, the cartridge slot includes first and second flexible fingers molded into the side of the cartridge housing.

19. The surgical instrument according to claim 18, wherein the first and second fingers are oriented parallel to the longitudinal axis of the cartridge module.

20. The surgical instrument according to claim 18, wherein the first finger is shaped and dimensioned to contact the detent of the knife.

21. The surgical instrument according to claim 18, wherein the second finger is shaped and dimensioned to contact the detent of the driver.

22. The surgical instrument according to claim 18, wherein cam surfaces are positioned along the edge of each of the first and second fingers.

23. The surgical instrument according to claim 22, wherein the location of the respective cam surfaces is determined by the desired position of the driver or knife during operation.

24. A surgical instrument adapted for applying a plurality of surgical fasteners to body tissue, the surgical instrument comprising:

a cartridge module including a cartridge housing containing a plurality of surgical fasteners and a knife, the cartridge module includes a driver disposed to push surgical fasteners out of the cartridge housing;

a firing mechanism associated with the cartridge housing for ejecting the surgical fasteners and the knife from the cartridge housing;

means for preventing undesired forward and rearward motion of the knife to prevent the knife from inadvertently moving; and wherein the driver includes a prefired position and a retracted position and means are operatively associated with the driver for securing the driver in the prefired position and for securing the driver in the retracted position.

25. The surgical instrument according to claim 24, wherein the means for preventing undesired forward and rearward motion of the knife includes a detent disposed to contact a mating detent of the cartridge module during the longitudinal travel of the knife and the means for securing the driver in the prefired position and the retracted position includes a detent disposed to contact at least one mating detent formed on the cartridge module.

26. The surgical instrument according to claim 25, wherein the cartridge housing includes a cartridge slot through which the detent of the knife extends, the cartridge slot includes first and second flexible fingers molded into the side of the cartridge housing.

27. The surgical instrument according to claim 26, wherein the first and second fingers are oriented parallel to the longitudinal axis of the cartridge module.

28. The surgical instrument according to claim 26, wherein the first finger is shaped and dimensioned to contact the detent of the knife.

29. The surgical instrument according to claim 26, wherein the second finger is shaped and dimensioned to contact the detent of the driver.

30. The surgical instrument according to claim 26, wherein cam surfaces are positioned along the edge of each of the first and second fingers.

31. The surgical instrument according to claim 30, wherein the location of the respective cam surfaces is determined by the desired position of the driver or knife during operation.

* * * * *